US012434104B2

(12) United States Patent
Tana et al.

(10) Patent No.: US 12,434,104 B2
(45) Date of Patent: Oct. 7, 2025

(54) METHOD FOR MANAGING THE USE OF AN EXERCISE MACHINE BY MULTIPLE USERS FOR PERFORMING PHYSICAL EXERCISES AND EXERCISE MACHINE IMPLEMENTING SUCH A METHOD

(71) Applicant: TECHNOGYM S.P.A., Cesena (IT)

(72) Inventors: Marcello Tana, Cesena (IT); Massimo Baldazzi, Cesena (IT); Mattia Generali, Cesena (IT); Stefano Santilli, Cesena (IT); Andrea Budelacci, Cesena (IT); Mauro Fabbri, Cesena (IT); Enrico Guidi, Cesena (IT)

(73) Assignee: TECHNOGYM S.P.A., Cesena (IT)

( * ) Notice: Subject to any disclaimer, the term of this patent is extended or adjusted under 35 U.S.C. 154(b) by 166 days.

(21) Appl. No.: 18/216,834

(22) Filed: Jun. 30, 2023

(65) Prior Publication Data

US 2024/0001201 A1 Jan. 4, 2024

(30) Foreign Application Priority Data

Jul. 1, 2022 (IT) ........................ 102022000014056

(51) Int. Cl.
*A63B 24/00* (2006.01)
*G16H 20/30* (2018.01)

(52) U.S. Cl.
CPC ......... *A63B 24/0087* (2013.01); *G16H 20/30* (2018.01); *A63B 2225/15* (2013.01); *A63B 2225/20* (2013.01); *A63B 2225/72* (2013.01)

(58) Field of Classification Search
CPC ............ A63B 24/0087; A63B 2225/15; A63B 2225/20; A63B 2225/72; A63B 22/0076; A63B 22/02; A63B 22/0605; A63B 23/0494; G16H 20/30; G16H 10/60; G16H 40/63
See application file for complete search history.

(56) References Cited

U.S. PATENT DOCUMENTS

2006/0189440 A1 8/2006 Gravagne
2007/0033069 A1* 2/2007 Rao .................... A63B 71/0622 482/8
2015/0190677 A1* 7/2015 Alsalem ................ G16H 20/30 700/91

OTHER PUBLICATIONS

Italian Search Report for Italian Patent Application No. 102022000014056 dated Feb. 3, 2023, Munich, DE.

* cited by examiner

*Primary Examiner* — Sundhara M Ganesan
(74) *Attorney, Agent, or Firm* — ArentFox Schiff LLP; Michael Fainberg

(57) ABSTRACT

A method for managing the use of an exercise machine by multiple users for performing physical exercises involves obtaining, following an authentication procedure by a first user, a code identifying the first user and information representative of the first user; storing the obtained code identifying the first user and information representative of the first user; obtaining, following an authentication procedure performed by at least one second user, a code identifying the at least one second user and information representative of the second user; storing the obtained code identifying the at least one second user and information representative of the at least one second user; and setting the exercise machine, following a selection of either the first user or the at least one second user for performing the respective physical exercise, based on either the code identifying the first user or the code identifying the at least one second user.

14 Claims, 13 Drawing Sheets

METHOD FOR MANAGING THE USE OF AN EXERCISE MACHINE BY MULTIPLE USERS FOR PERFORMING PHYSICAL EXERCISES AND EXERCISE MACHINE IMPLEMENTING SUCH A METHOD

CROSS-REFERENCE TO RELATED APPLICATION

This application claims priority to Italian Patent Application No. 102022000014056 filed on Jul. 1, 2022, the contents of which are incorporated by reference in their entirety.

FIELD OF THE INVENTION

The present invention relates to the fitness field, and in particular, to a method for managing the use of an exercise machine by multiple users for performing physical exercises, and to an exercise machine implementing such a method.

BACKGROUND OF THE INVENTION

Typically, for using an exercise machine a user logs in to set up a respective personal profile on the exercise machine so that the exercise machine can upload the respective workout program and, either during or at the end of the workout, can store the user's performance data to send it to a remote (cloud-based) server, which keeps track of the user's workout history in a personal area of the user associated with the respective personal profile.

If there are multiple users, for example in a gym, whose workout program includes the use of the same exercise machine, a second user, at the end of the use of the exercise machine by a first user, will in turn log-in so that the exercise machine is set to the personal profile of the second user, actually losing the setting previously kept for the first user.

In light of this, the workout of multiple users on the same exercise machine certainly appears impractical and with obvious time delays at the start of the workout due to the waiting time for the authentication procedure.

This is even more amplified if an exercise machine is used in an intense training circuit in which avoidable waiting times cause muscle cooling and risk worsening the user's performance and compromising an optimal workout.

Moreover, attempting to obviate this drawback by expanding the number of exercise machines is impractical in a gym for reasons of logistics, space, and obviously cost.

Therefore, the need is strongly felt to have a method for managing the use of an exercise machine by multiple users for performing a physical exercise which allows the use of the exercise machine by multiple users in a simple, user-friendly, and especially timely manner, ensuring that each user's workout is as high-performing as possible.

SUMMARY

It is the object of the present invention to devise and provide a method of managing the use of an exercise machine by multiple users for performing a physical exercise which will at least partially obviate the drawbacks complained of hereto with reference to the prior art, in particular which will allow the use of the exercise machine by multiple users in a simple, user-friendly and especially timely manner, ensuring that each user's workout is as high-performing as possible.

Such an object is achieved by a method as described and claimed herein.

Preferred embodiments of the method are also described.

The present invention also relates to an exercise machine implementing such a method, and a system comprising such an exercise machine.

BRIEF DESCRIPTION OF THE DRAWINGS

Further features and advantages of the method and of the exercise machine according to the invention will be apparent from the following description of preferred embodiments, given by way of non-limiting indication, with reference to the accompanying drawings, in which.

It should be noted that, in the figures, equivalent or similar elements are indicated by the same numeric and/or alphanumeric references.

DETAILED DESCRIPTION

An exercise machine 1 usable by a user to perform a physical exercise according to the present invention is now described with reference to the figures.

"Physical exercise" means a category within the physical activity, quantified by volume, intensity, and frequency in which planned movements are structured in a repetitive manner to allow a user to improve and/or keep one or more components of the physical fitness.

The exercise machine 1 can be any exercise machine usable by a user to perform a physical exercise, such as an exercise machine for a cardiovascular workout, a strength exercise machine, or an exercise machine in which both a cardiovascular workout and strength exercises can be performed.

Examples of the exercise machine 1 are shown in FIGS. 1*a*-1*f*.

Figure 1B:
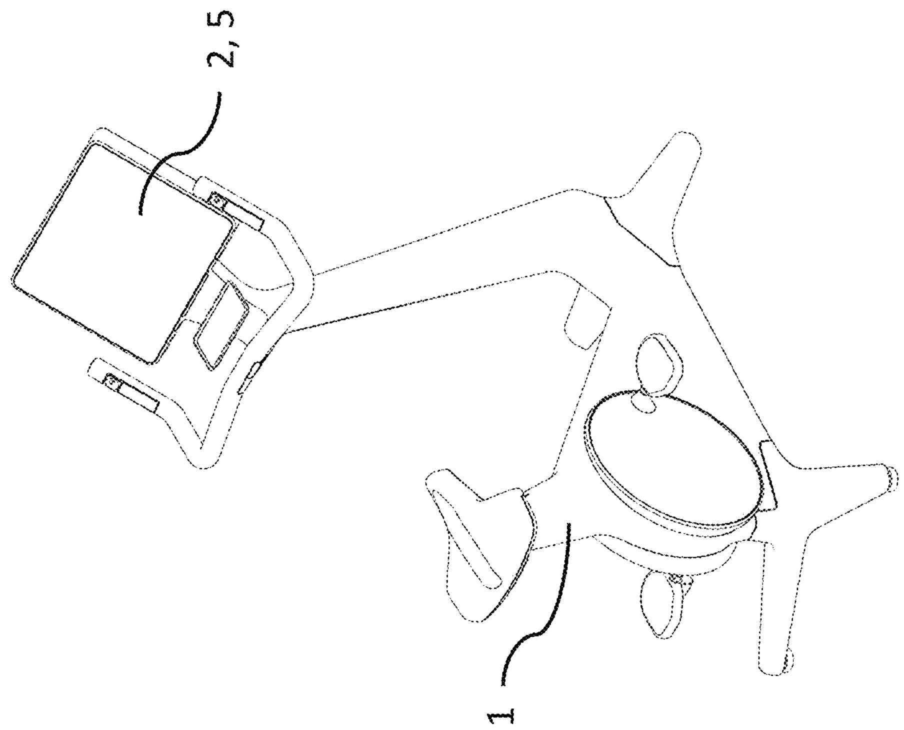
FIGS. 1*a*, 1*b*, 1*c*, 1*d*, 1*e*, and 1*f* show examples of an exercise machine usable by a user for performing a physical exercise.
Figure 1A:
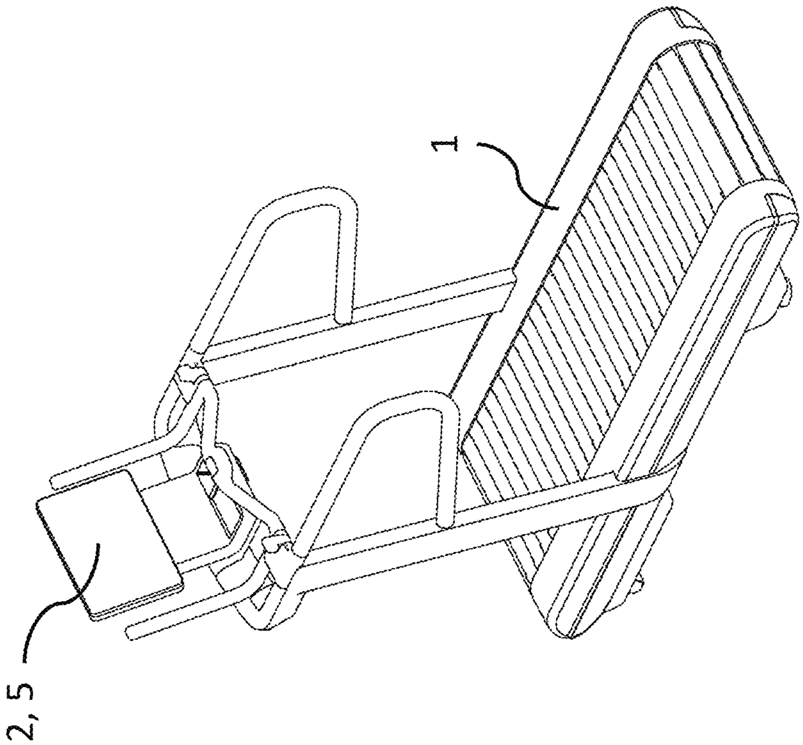

FIG. 1*a* shows a treadmill.

FIG. 1*b* shows a bike or exercise bike.

Figure 1C:
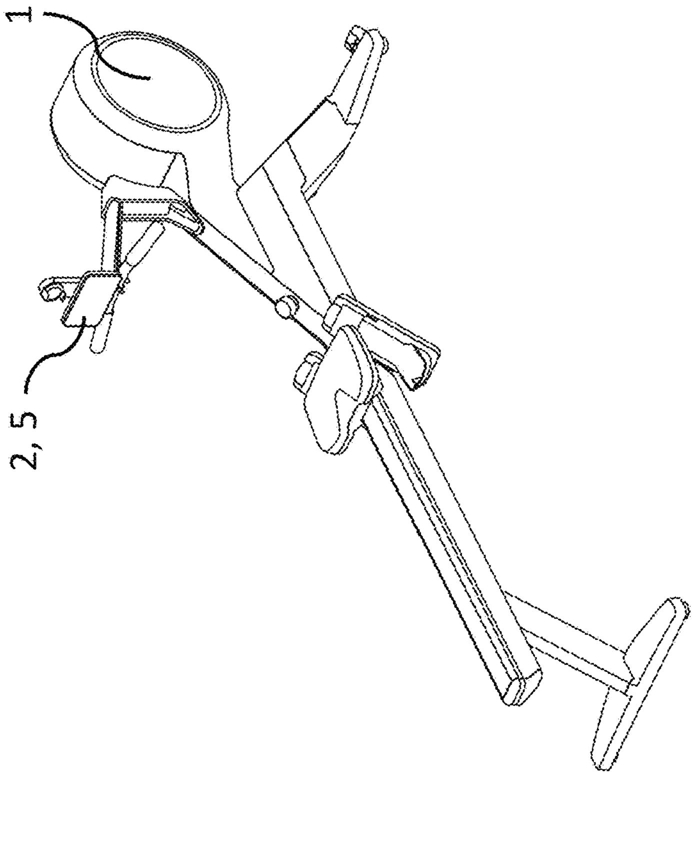

FIG. 1*c* shows a rowing machine.

Figure 1D:
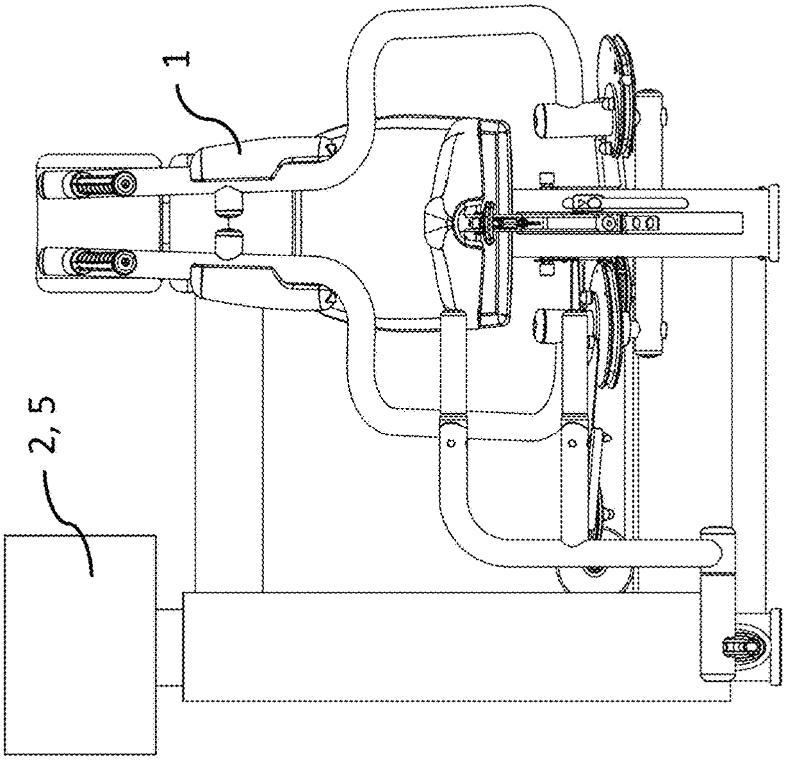

FIG. 1*d* shows an upper limb strength exercise machine, e.g., a "pectoral machine".

Figure 1E:
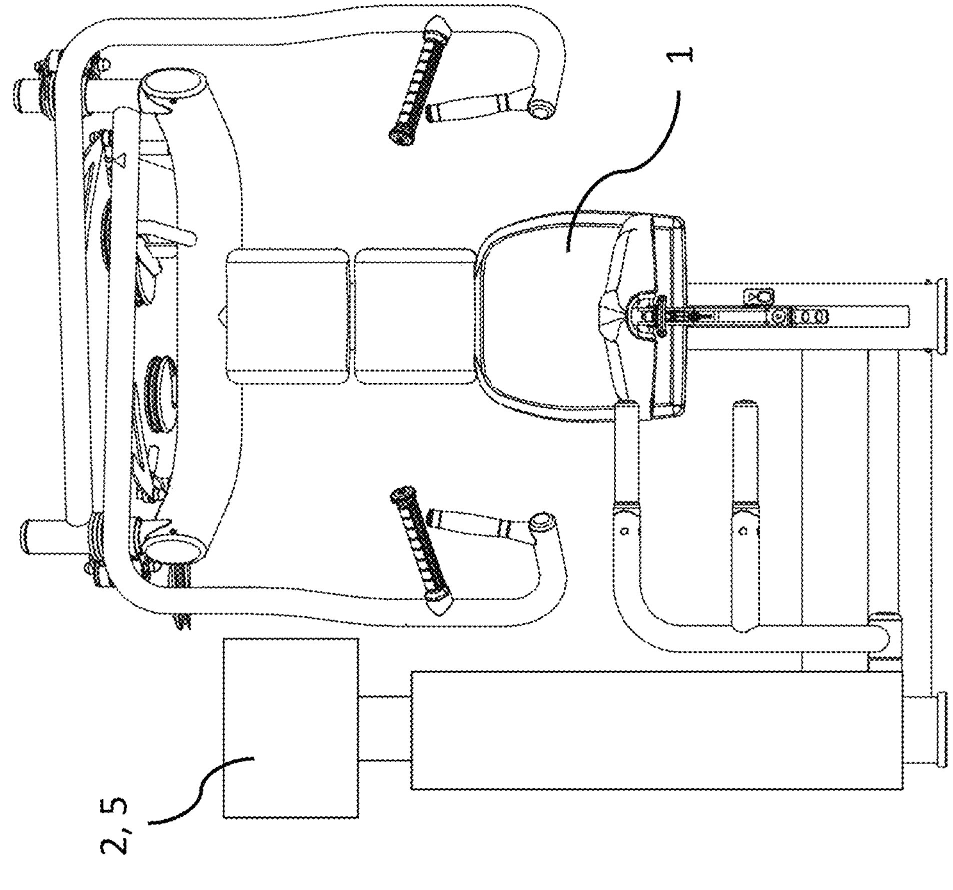

FIG. 1*e* shows an example of an upper limb strength exercise machine, e.g., a "chest press".

Figure 1F:
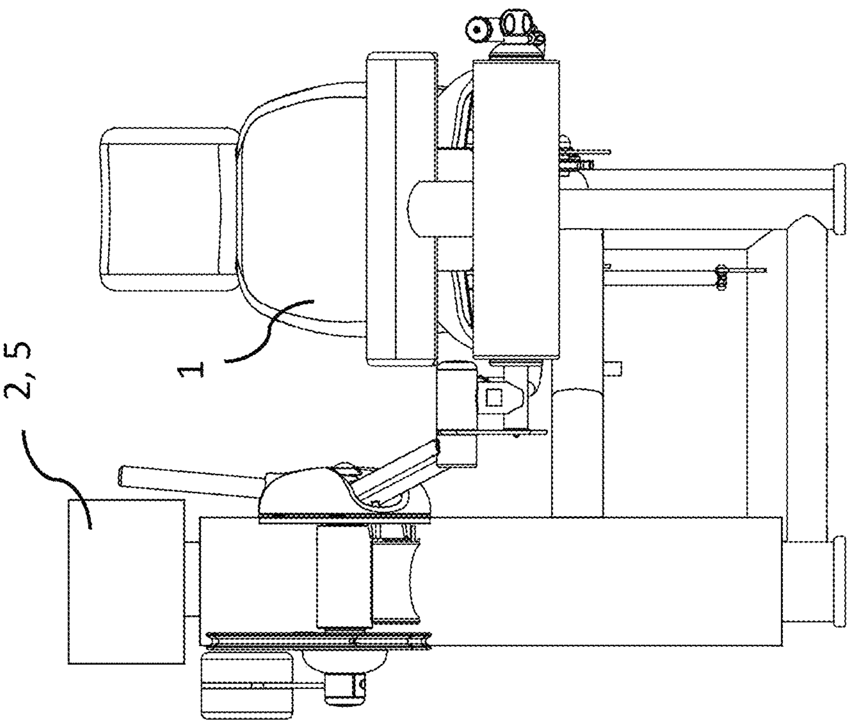

FIG. 1*f* shows an example of a lower limb strength exercise machine, e.g., a "leg extension" machine.

In the case of a cardio-fitness machine (treadmill, bike or exercise bike, rowing machine), the movements involved in a physical exercise can be:

- running or walking (treadmill);
- push, sled or pull training with a number of sets, a number of repetitions per set, and a load in opposition to a user's action (treadmill);
- pedaling (bike or exercise bike);
- cyclic movement of upper and lower limbs to simulate rowing, size of the load to be moved (rowing machine).

In the case of a strength exercise machine, the movements involved in a physical exercise can be:

- concentric movement and eccentric movement of the upper limbs with a number of sets, a number of repetitions per set, and size of the load to be moved;
- concentric movement and eccentric movement of the lower limbs with a number of sets, a number of repetitions per set, and size of the load to be moved.

Figure 2B:
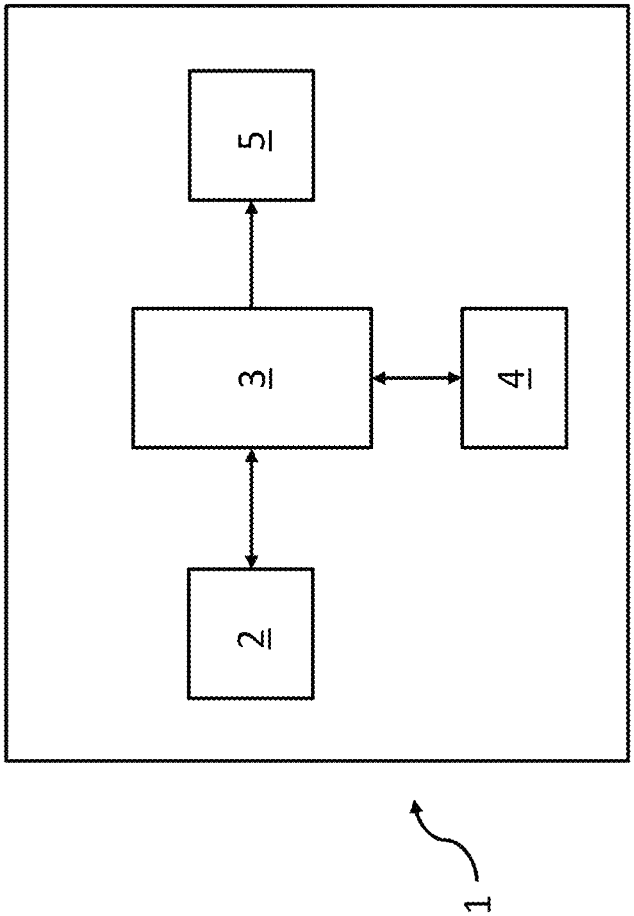
FIGS. 2*a* and 2*b* each show, by means of a block diagram, an exercise machine implementing a method for managing the use of an exercise machine by multiple users for performing a physical exercise, according to the present invention.
Figure 2A:
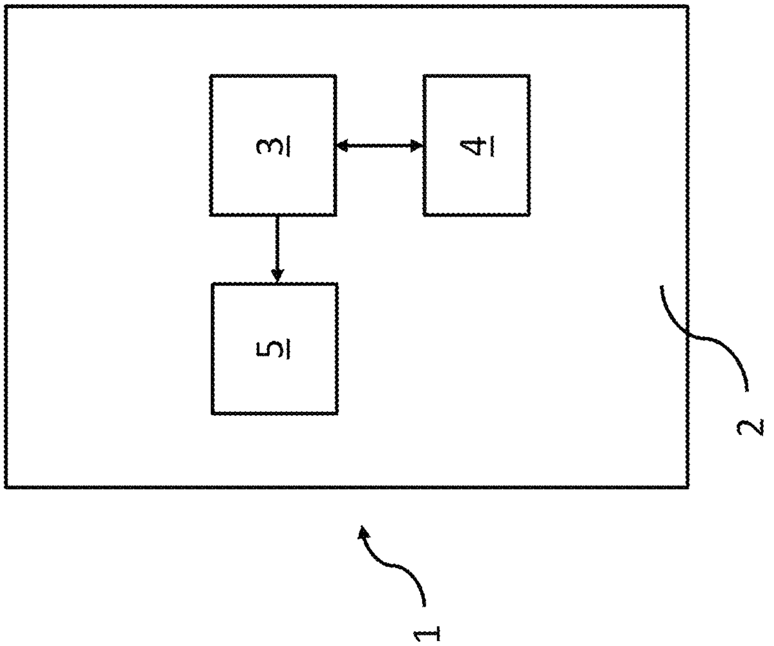

The following description, with reference in particular to FIGS. 2*a* and 2*b*, applies to any of the exercise machines 1 listed above.

The exercise machine 1 comprises a user interface 2 configured to allow a user to interact with the exercise machine 1.

The exercise machine 1 comprises a data processing unit 3, e.g., a microprocessor or a microcontroller.

The user interface 2 is operatively connected to the data processing unit 3 of the exercise machine 1.

The exercise machine 1 further comprises a local memory unit 4, operatively connected to the data processing unit 3.

The local memory unit 4 can be either internal or external (as shown in FIGS. 2*a* and 2*b*, for example) with respect to the data processing unit 3.

It should be noted that the local memory unit 4 is configured to store one or more program codes executable by the data processing unit 3 and data generated and processed after the execution of said one or more program codes.

The data processing unit 3 is configured to control the operation of the exercise machine 1.

Moreover, the data processing unit 3 is configured to carry out steps of a method for managing the use of an exercise machine by multiple users for performing a physical exercise according to the present invention, as described hereinbelow.

The exercise machine 1 further comprises a display module 5, e.g., a display, operatively connected to the data processing unit 3.

The display module 5 is usable by the user during the interaction with the user interface 2.

Indeed, the display module 5 is configured to show to the user contents representative of the use of the exercise machine 1, e.g., identification screen, initial menu screen for setting up the workout, screen with parameters and/or graphics being updated while the exercise is being performed, workout summary screen, and so on.

Moreover, as described hereinbelow, the display module 5 is configured to show screens to the user which can be displayed while carrying out the method for managing the use of an exercise machine by multiple users for performing a physical exercise, object of the present invention.

In this respect, examples of screens which can be displayed by the display module 5 will be described hereinbelow with reference to FIGS. 4*a*-4*d* and to FIGS. 4*e*-4*g*.

The data processing unit 3, the local memory unit 4, and the display module 5 can be one or more, either internal or external with respect to the user interface 2 of the exercise machine 1.

According to a further embodiment shown in FIG. 2*a*, the data processing unit 3, the local memory unit 4, and the display module 5 are integrated inside the user interface 2.

In an embodiment, as an alternative to the preceding one and shown in FIG. 2*b*, the data processing unit 3, the local memory unit 4, and the display module 5 are external with respect to the user interface 2.

In an embodiment, in which the display module 5 is integrated into the user interface 2, the display module 5 can coincide, in whole or in part, with the user interface.

In an embodiment, the user interface 2 can be of the touchscreen type.

In a further embodiment, as an alternative to the preceding one, the user interface 2 can be a mechanical keyboard.

In the examples in FIGS. 1*a*-1*f*, the user interface 2 is preferably of the touchscreen type and the display module 5 entirely coincides with the user interface 2.

Figure 3:
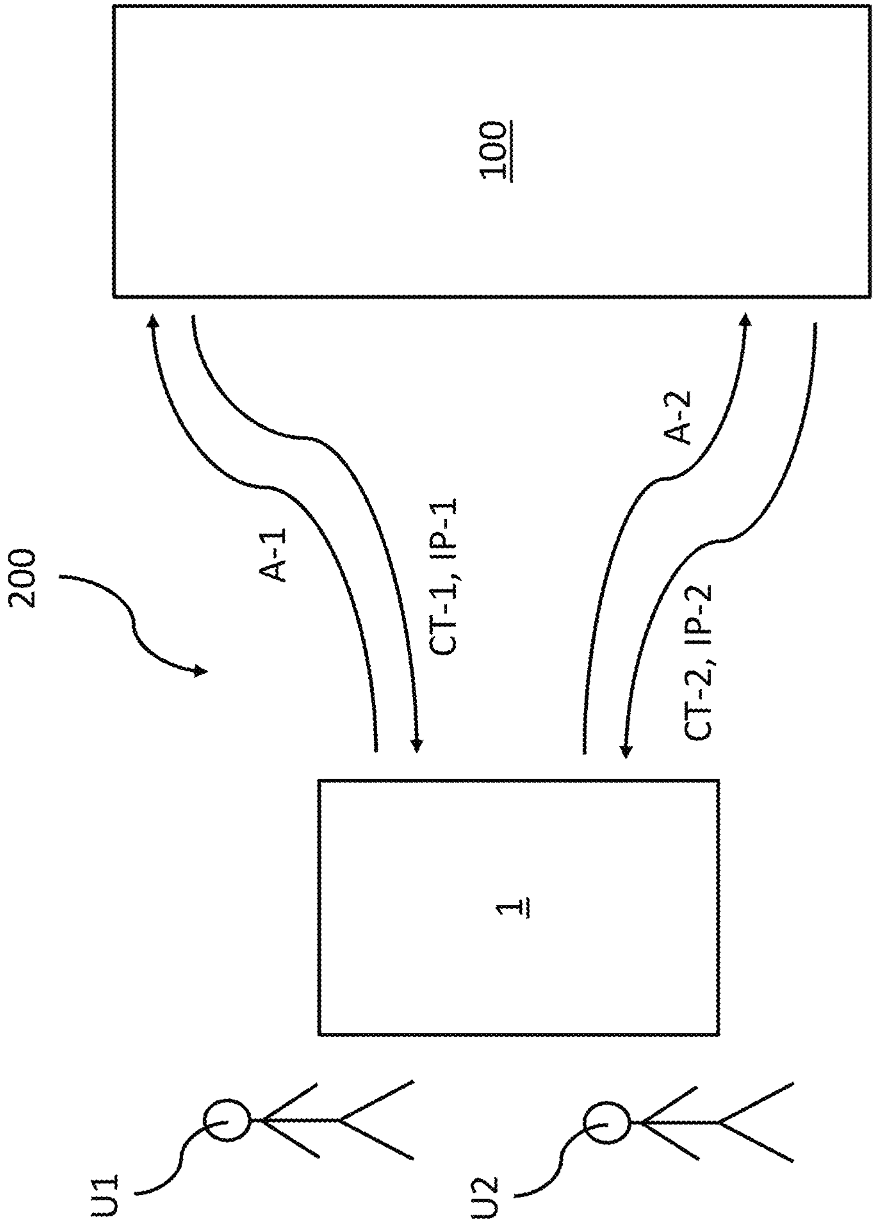
FIG. 3 diagrammatically shows a system comprising an exercise machine configured to implement the method for managing the use of an exercise machine by multiple users for performing a physical exercise, according to the present invention.

Returning to the functionality of the data processing unit 3 for managing the use of an exercise machine by multiple users for performing a physical exercise, the data processing unit 3 is configured to obtain from a remote electronic processor 100, diagrammatically shown in FIG. 3, operatively associated with exercise machine 1, following an authentication (or login) procedure A-1 performed on the exercise machine 1 by a first user U1 having a respective user profile, a code CT-1 identifying the first user U1 and one or more pieces of information IP-1 representative of the user profile of the first user U1 for using the exercise machine 1 for a respective physical exercise.

The code CT-1 identifying the first user U1 can be a temporary unique identification code (e.g., an alphanumeric string) assigned to the first user U1 following the authentication on the exercise machine 1 and from the authentication of the first user on exercise machine 1 is then stored in the local memory unit 4 of the exercise machine 1 (as will also be reiterated hereinbelow) until a log-out procedure of the first user U1 is performed.

Alternatively, the i code CT-1 identifying the first user U1 can be an existing unique identification code (e.g., an alphanumeric string) already assigned to the first user U1 which, following the authentication of the first user U1 on the exercise machine 1, is then stored in the local memory unit 4 of the exercise machine 1 (as will also be reiterated hereinbelow) until a log-out procedure of the first user U1 is performed.

Examples of said one or more pieces of information IP-1 representative of the user profile of the first user U1 for using the exercise machine 1 for a respective physical exercise comprise: the user's photo or graphic representation (avatar), age, gender, weight, training level, athletic training level, 1-RM, ROM, workout program to be carried out with control/setting data of the exercise machine, and so on.

The authentication procedure A-1 can occur according to any of the following modes: by means of a handheld device, smartphone or tag/RFID, or manually, through a code or other identification data, or by fingerprint, voice recognition, face ID, and so on.

Following the authentication procedure A-1, the data processing unit 3 of the exercise machine 1 is configured to send to the remote electronic processor 100 an authentication request of the first user U1, and the remote electronic processor 100, in response to such an authentication request, will send to the data processing unit 3 of the exercise machine 1 the code CT-1 identifying the first user U1 and the one or more pieces of information IP-1 representative of the user profile of the first user U1 for using the exercise machine 1 for a respective physical exercise.

The data processing unit 3 of the exercise machine 1 is configured to store in the local memory unit 4 of the exercise machine 1 the obtained code CT-1 identifying the first user U1 and said obtained one or more pieces of information IP-1 representative of the first user.

The data processing unit 3 of the exercise machine 1 is further configured to obtain from the remote electronic processor 100, following an authentication procedure A-2 performed on the exercise machine 1 by at least one second user U2 having a respective user profile, a code CT-2 identifying the at least one second user U2 and one or more pieces of information IP-2 representative of the user profile of the second user U2 for using the exercise machine 1 for a respective physical exercise.

The code CT-2 identifying the at least one second user U2 can be a temporary unique identification code (e.g., an alphanumeric string) assigned to the at least one second user U2 following the authentication on the exercise machine 1 and then stored in the local memory unit 4 of the exercise machine 1 (as will also be reiterated hereinbelow) until a log-out procedure of the at least one second user U2 is performed.

Alternatively, the code CT-2 identifying the at least one second user U2 can be an existing unique identification code (e.g., an alphanumeric string) already assigned to the second user U2 which, following the authentication of the second user U2 on the exercise machine 1, is then stored in the local memory unit 4 of the exercise machine 1 (as will also be reiterated hereinbelow) until a log-out procedure of the at least one second user U2 is performed.

Examples of said one or more pieces of information IP-2 representative of the user profile of the second user U2 for using the exercise machine 1 for a respective physical exercise comprise: age, gender, weight, training level, athletic training level, 1-RM, ROM, workout program to be carried out with control/setting data of the exercise machine, and so on.

The authentication procedure A-2 can also occur according to any of the following modes: by means of a handheld device, smartphone or tag/RFID, or manually, through a code or other identification data, or by fingerprint, voice recognition, face ID, and so on.

Following the authentication procedure A-2, the data processing unit 3 of the exercise machine 1 is configured to send to the remote electronic processor 100 a request for authentication of the at least one second user U2, and the remote electronic processor 100, in response to such an authentication request, will send to the data processing unit 3 of the exercise machine 1 the code CT-2 identifying the at least one second user U2 and the one or more pieces of information IP-2 representative of the user profile of the second user U2 for using the exercise machine 1 for a respective physical exercise.

The data processing unit 3 of the exercise machine 1 is configured to store in the local memory unit 4 of the exercise machine 1 the obtained code CT-2 identifying the at least one second user U2 and said obtained one or more one or more pieces of information IP-2 representative of the at least one second user U2.

According to the present invention, the data processing unit 3 of the exercise machine 1 is configured to set the exercise machine 1, following a selection of one from either the first user U1 or the at least one second user U2 carried out on the exercise machine 1, to be used for performing the respective physical exercise by one from either the first user U1 or the at least one second user U2, based on one from either the code CT-1 identifying the first user U1 or the code CT-2 identifying the at least one second user U2 corresponding to the selected user from either the first user U1 or the at least one second user U2.

In an embodiment, in combination with the preceding one, the data processing unit 3 of the exercise machine 1 is configured to set the exercise machine 1 by loading on the exercise machine 1 the respective user profile and a respective physical exercise program corresponding to the selected user from either the first user U1 or the at least one second user U2, based on the one from either the code CT-1 identifying the first user U1 or the code CT-2 identifying the at least one second user U2 corresponding to the selected user from either the first user U1 or the at least one second user U2.

"Loading the set physical exercise program" of a user means loading, by the data processing unit 3 of the exercise machine 1, information representative of the set physical exercise program of a user.

By way of example, if the exercise machine is a strength exercise machine, such information representative of the set physical exercise program of a user comprises the size and type of the load to be moved, the number of repetition sets, the number of repetitions within a set, the exercise performance speed, and so on.

By way of example, if the exercise machine is a cardiovascular exercise machine, such information representative of the set physical exercise program of a user comprises the workout speed, the slope of the exercise surface, e.g., in the case of a treadmill, the pedaling speed, the power to be developed, the resistance to pedaling, e.g., in the case of a bike or recline, the number of repetition sets, the number of repetitions within a set, the size of the load in opposition to the user's action, e.g., in the case of pushing exercises on a treadmill, and so on.

According to an embodiment, in combination with any of those described above, the data processing unit 3 of the exercise machine 1 is further configured to query the remote electronic processor 100 during the use of the exercise machine 1 for performing the respective physical exercise by the selected user from either the first user U1 or the at least one second user U2, using either the code CT-1 identifying the first user U1 or the code CT-2 identifying the at least one second user U2 corresponding to the selected user from either the first user U1 or the at least one second user U2, stored in the local memory unit 4 of the exercise machine 1.

In greater detail, the data processing unit 3 of the exercise machine 1 is further configured to query the remote electronic processor 100 in real time, at set instants of sampling time, to retrieve setting and control data of the exercise machine 1 provided by the training program running while the selected user performs the physical exercise.

According to an embodiment, in combination with any of the preceding ones, the data processing unit 3 of the exercise machine 1 is configured to store, during the use of the exercise machine 1, data representative of the respective physical exercise performed by the user with the exercise machine 1.

According to an embodiment, in combination with the preceding one, the data processing unit 3 of the exercise machine 1 is configured to store data representative of the respective physical exercise performed by the user with the exercise machine 1 in the local memory unit 4 of the exercise machine 1 and/or in the remote electronic processor 100.

According to an embodiment, in combination with the preceding one, the data processing unit 3 of the exercise machine 1 is configured to store data representative of a group of movements provided by the physical exercise performed by the user with the exercise machine 1 from when the data processing unit 3 of the exercise machine 1 has selected such a user from either the first user U1 or the at least one second user U2, for using the exercise machine 1 to when the data processing unit 3 of the exercise machine 1 has then selected the other user from either the first user U1 or the at least one second user U2 for using the exercise machine 1.

The group of movements depends on the type of exercise machine used and/or the type of physical exercise performed.

For example, a group of movements can be:

running over a set distance in the case of the treadmill;

pedaling over a set distance in the case of a bike;

a set of repetitions in the case of sled on a treadmill;

rowing over a set distance on a rowing machine;

a set of repetitions on a strength exercise machine.

According to an embodiment, in combination with any of the preceding ones, where if the user, from either the first user U1 or the at least one second user U2, has already been selected once for using the exercise machine 1 and has performed a first group of movements provided by the physical exercise performed by the selected user and the data processing unit 3 of the exercise machine 1 has stored first data representative of the first group of movements provided by the physical exercise performed by the selected user, the data processing unit 3 of the exercise machine 1 is configured to:

- retrieve, when the data processing unit 3 of the exercise machine 1 selects the same user again from either the first user U1 or the at least one second user U2, for using the exercise machine 1, the previously stored first data representative of the first group of movements provided by the physical exercise performed by the selected user;
- set the exercise machine 1 to be used for performing a second group of movements provided by the physical exercise performed by the same selected user, based on the previously stored first data representative of the first group of movements provided by the physical exercise performed by the selected user.

According to an embodiment, in combination with any of those described above, the data processing unit 3 of the exercise machine 1 is configured to select one from either the first user U1 or the at least one second user U2 based on a received manual command.

For example, as will be described below, the manual selection command can be provided to the data processing unit 3 of the exercise machine 1 by means of the user interface 2 of the exercise machine 1 by one of the users logged-in on the exercise machine 1, thus the first user U1 and the at least one second user U2, or by a third party, e.g., a personal trainer.

According to a further embodiment, in combination with any of those described above, the data processing unit 3 of the exercise machine 1 is configured to select one from either the first user U1 or the at least one second user U2 automatically based on a set workout program provided for the first user U1 and a set workout program provided for the at least one second user U2.

In other words, from the set training programs provided for the first user U1 and for the at least one second user U2, the data processing unit 3 is able of automatically selecting one of the first user U1 and the at least a second U2 user.

For example, once the first user U1 completes the assigned repetitions (provided by the set training program) on a strength exercise machine or completes an assigned distance to walk (provided by the set training program) on a treadmill, the data processing unit 3 is able of automatically selecting the at least one second user U2.

According to a further embodiment, in combination with any of those described above, the data processing unit 3 of the exercise machine 1 is configured to automatically carry out the selection of either the first user U1 or the at least one second user U2 if only one of either the first user U1 or the at least one second user U2 (e.g., the first user U1) has already performed the authentication procedure on the exercise machine 1 and the other of either the first user U1 or the at least one second user U2 (e.g., the at least one second user U2) performs the authentication procedure on the exercise machine 1 for the first time.

In other words, the data processing unit 3 is able of automatically selecting one of the first user U1 and the at least one second user U2 if one of the first user U1 and the at least one second user U2 (for example, the at least one second user U2) performs the authentication procedure on the exercise machine 1 for the first time while only the other between the first user U1 and the at least one second user U2 (for example, the first user U1) has already carried out the authentication procedure on exercise machine 1.

In this case, following the first authentication of the at least one second user U2, the data processing unit 3 of the exercise machine 1 is configured to automatically set the user profile corresponding to the at least one second user U2 on the exercise machine 1.

According to a further embodiment, in combination with any of those described above, the data processing unit 3 of the exercise machine 1 is configured to automatically carry out the selection of one from either the first user U1 or the at least one second user U2 if both the first user U1 and the at least one second user U2 has already performed the authentication procedure on the exercise machine 1 and one from either the first user U1 or the at least one second user U2 performs a log-out procedure from the exercise machine 1.

In other words, if both the first user U1 and the at least one second user U2 are authenticated on the exercise machine 1 and one of the first user U1 and the at least one second user U2 executes the log-out procedure, the data processing unit 3 is configured to automatically perform the selection of the other between the first user U1 and the at least one second user U2 so as to maintain the setting of the exercise machine 1 for the user who remained authenticated.

In this way, optimal and optimized use of the exercise machine 11 is guaranteed.

For example, if the first user U1 performs the log-out procedure, the data processing unit 3 of the exercise machine 1 is configured to select the at least one second user U2 and automatically set the user profile corresponding to the at least one second user U2 on the exercise machine 1.

According to an embodiment, in combination with the preceding one, if there are multiple users logged-in on the exercise machine 1, in addition to the first user U1 and at least one second user U2, the data processing unit 3 of the exercise machine 1 is configured to automatically carry out the selection of one of the users who performed the authentication procedure on the exercise machine 1 if one of the users performs a log-out procedure from the exercise machine 1, based on a set priority criterion.

For example, the data processing unit 3 of the exercise machine 1 can automatically select the user, from those remaining logged in on the exercise machine 1, who had first performed the authentication procedure.

According to a further embodiment, in combination with any of those described above, the data processing unit 3 of the exercise machine 1 is configured to perform a log-out procedure from the exercise machine 1 for both the first user U1 and the at least one second user U2.

According to a further embodiment, in combination with the preceding one, the data processing unit 3 of the exercise machine 1 is configured to perform the log-out procedure simultaneously for the first user U1 and the at least one second user U2.

According to a further embodiment, as an alternative to the preceding one, the data processing unit 3 of the exercise machine 1 is configured to perform the log-out procedure at different time instants of either the first user U1 or the at least one second user U2.

According to an embodiment, in combination with any of those described above, the data processing unit 3 of the exercise machine 1 is configured to display on the display module 5 of the exercise machine 1 graphic screens representative of the management of the use of the exercise machine 1 by multiple users for performing a physical exercise.

With reference to FIGS. 4*a*-4*d*, examples of graphic screens which can be displayed on the display module 5 of the exercise machine 1 are now described, when the exercise machine 1 is for a cardiovascular workout, e.g., a treadmill.

It should be noted that these examples refer to the embodiment of the exercise machine 1 in which the display module 5 coincides with the user interface 2 of the exercise machine 1 which, preferably of the touchscreen type, allows a user to interact with and impart commands to the exercise machine 1.

Figure 4A:
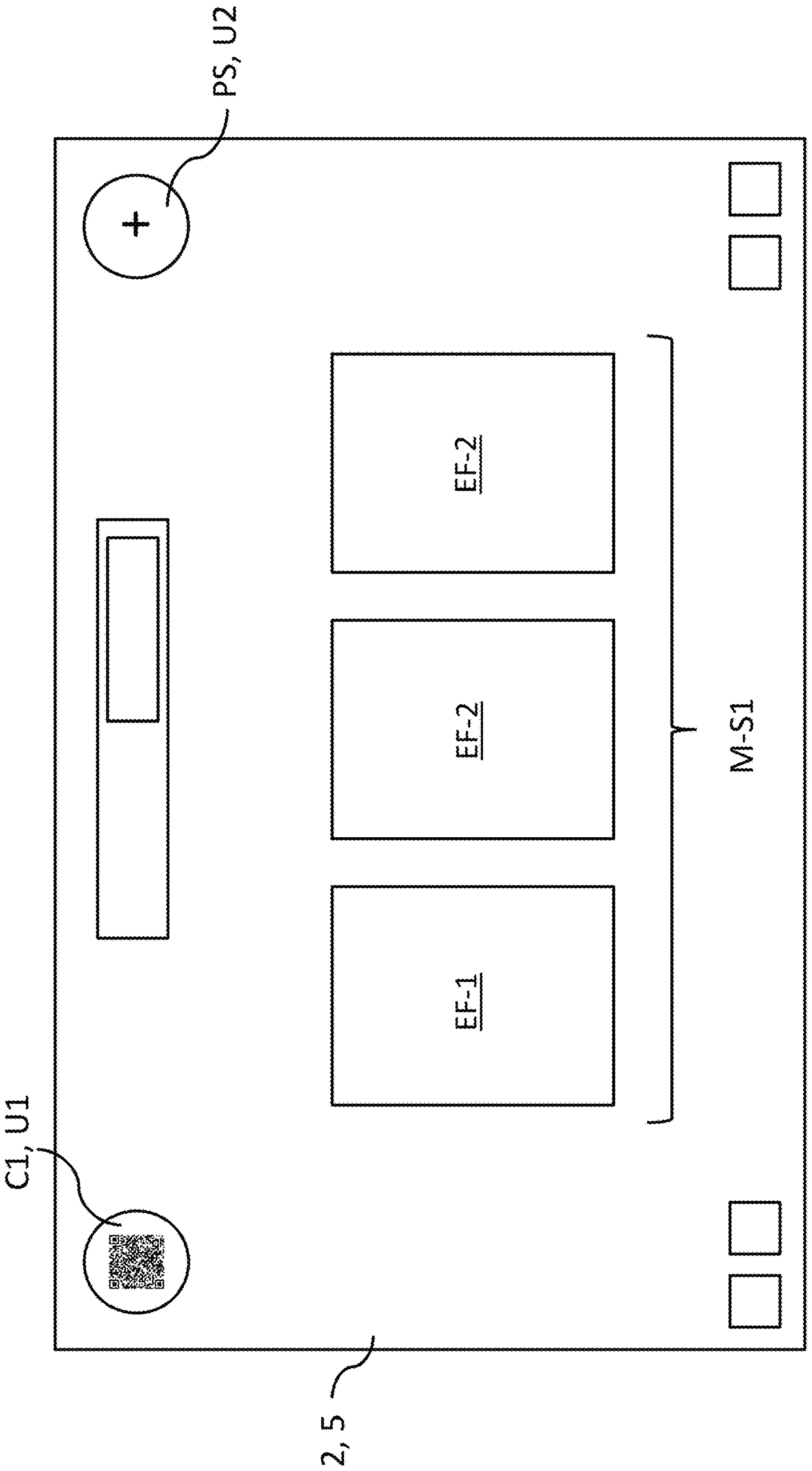
FIGS. 4*a*-4*d* diagrammatically show graphic screens which can be displayed on a display module of an exercise machine implementing the method for managing the use of an exercise machine by multiple users according to the present invention, during the execution of such a method.

With reference to FIG. 4*a*, a first graphic screen which can be displayed on the display module 5 of the exercise machine 1 comprises:

- a first authentication enabling command C1 which can be selected by a first user U1 (e.g., the first user U1) to perform an authentication procedure on the exercise machine 1;
- a first menu M-S1 of choices from a plurality of physical exercises EF-1, EF-2, EF-3 provided by the exercise machine 1 for the workout (for example, if the exercise machine 1 is a treadmill: first physical exercise EF-1: running; second physical exercise EF-2: sled training; third exercise EF-3: parachute training; if the exercise machine 1 is a strength exercise machine: first exercise EF-1: isotonic type resistance; second exercise EF-2: viscous type resistance; third exercise EF-3: elastic type resistance); and
- a command PS to add at least one second U2 user to a respective authentication procedure on the exercise machine 1.

Figure 4B:
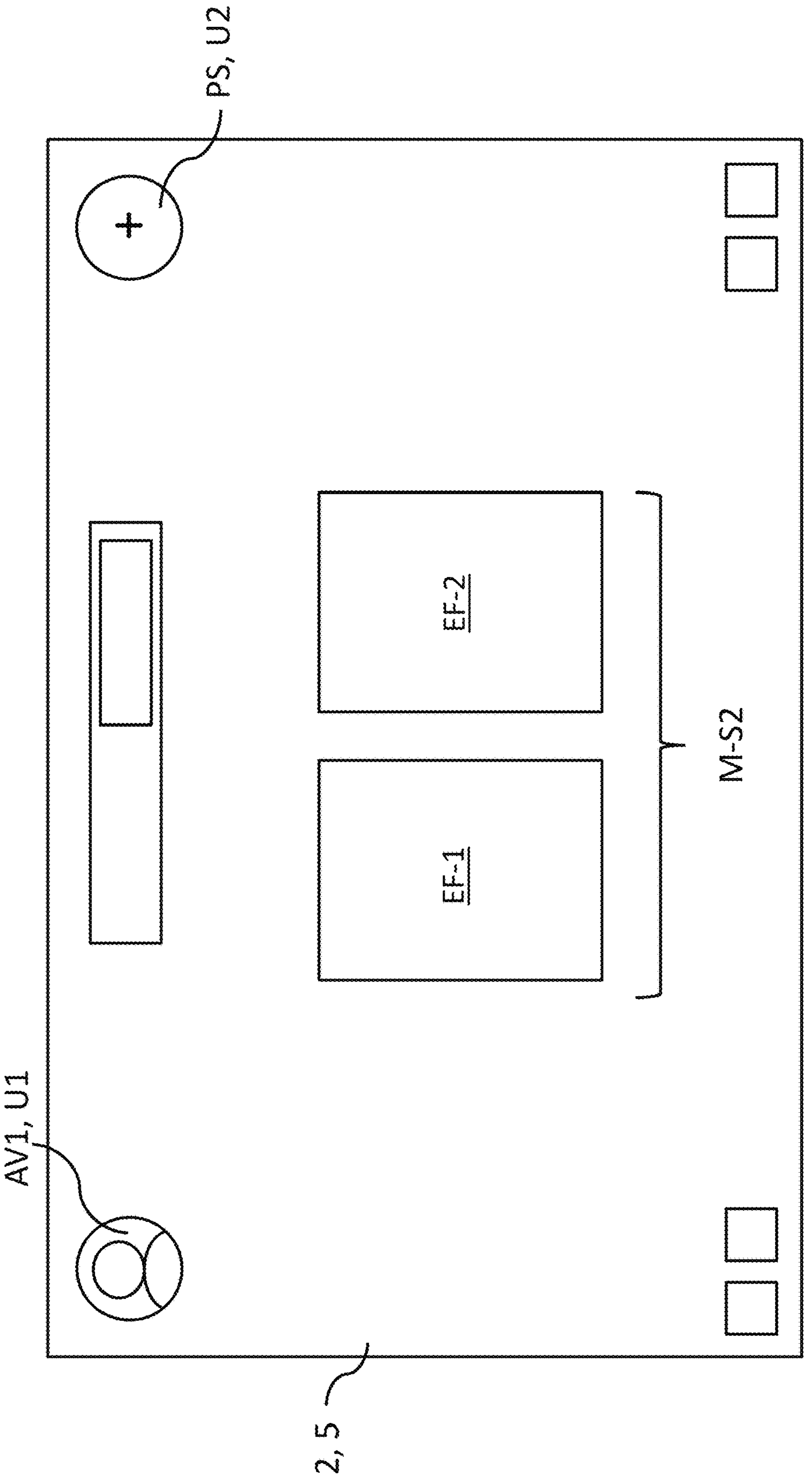

With reference to FIG. 4*b*, a second graphic screen which can be displayed on the display module 5 of the exercise machine 1 is shown.

The second graphic screen can be displayed on the display module 5 of the exercise machine 1 following the authentication of the first user U1 on the exercise machine 1 after the first user U1 has performed the authentication procedure on the exercise machine 1.

The second graphic screen which can be displayed on the display module 5 of the exercise machine 1 comprises:

- a first graphic representation (avatar) AV1 of the first user U1 logged-in on the exercise machine 1;
- a second menu M-S2 of choices from a plurality of physical exercises EF-1, EF-2, which can be selected by the first user U1 for the physical exercise with the exercise machine 1 (for example, if the exercise machine 1 is a treadmill: first physical exercise EF-1: running; second physical exercise EF-2: sled training; if the exercise machine 1 is a strength exercise machine: first exercise EF-1: isotonic type resistance; second exercise EF-2: viscous type resistance); and
- a command PS to add at least one second U2 user to a respective authentication procedure on the exercise machine 1.

Figure 4C:
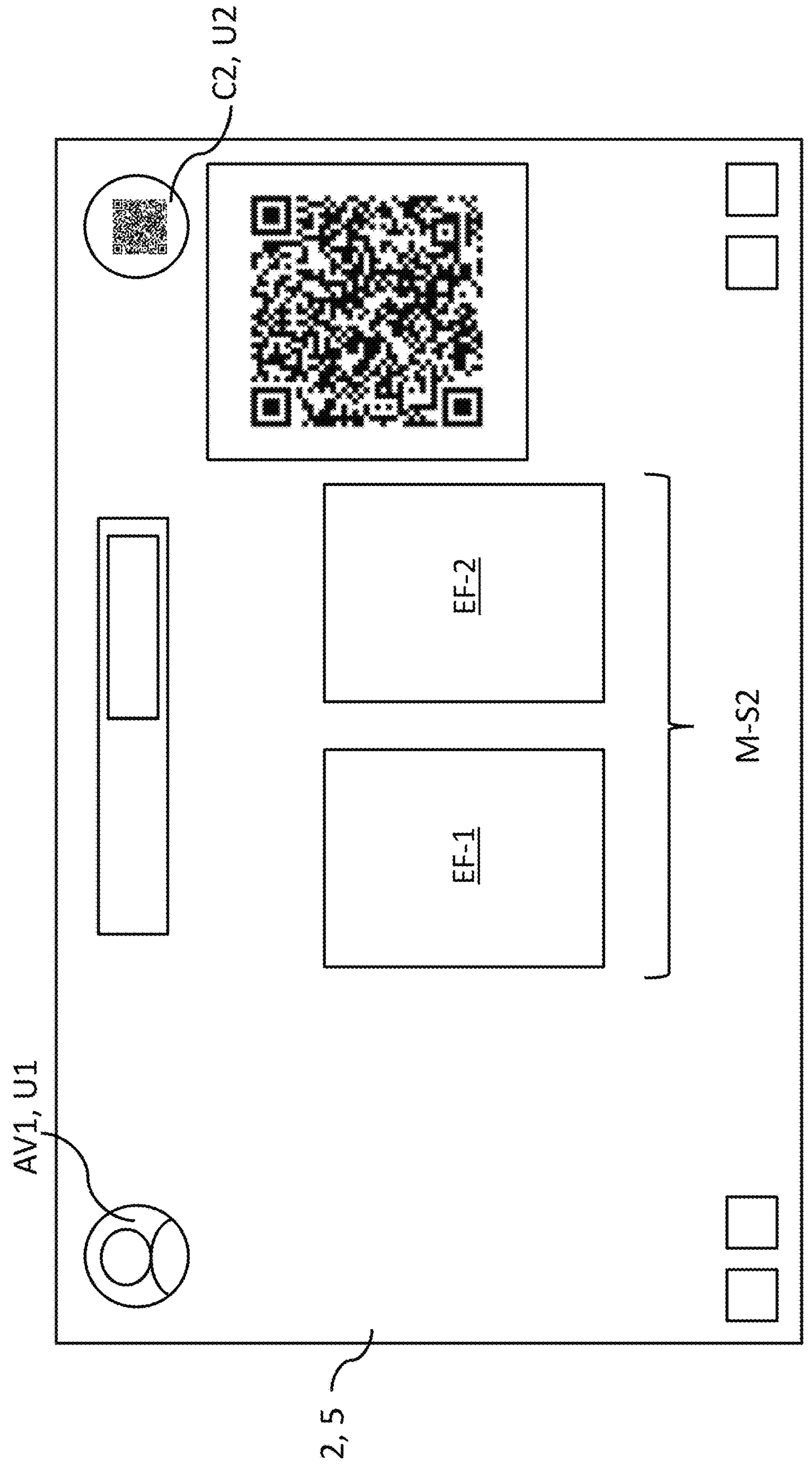

With reference to FIG. 4*c*, a third graphic screen which can be displayed on the display module 5 of the exercise machine 1 is shown.

The third graphic screen can be displayed on the display module 5 of the exercise machine 1 upon pressing the command PS of adding at least one second user U2 to a respective authentication procedure on the exercise machine 1.

The third graphic screen which can be displayed on the display module 5 of the exercise machine 1 comprises:

- a first graphic representation (avatar) AV1 of the first user U1 logged-in on the exercise machine 1;
- the second menu M-S2 of choices from a plurality of physical exercises EF-1, EF-2 which can be selected by the first user U1 for the physical exercise with the exercise machine 1; and
- a second authentication enabling command C2 which can be selected by said at least one second user U2 to perform, in turn, an authentication procedure on the exercise machine 1.

Figure 4D:
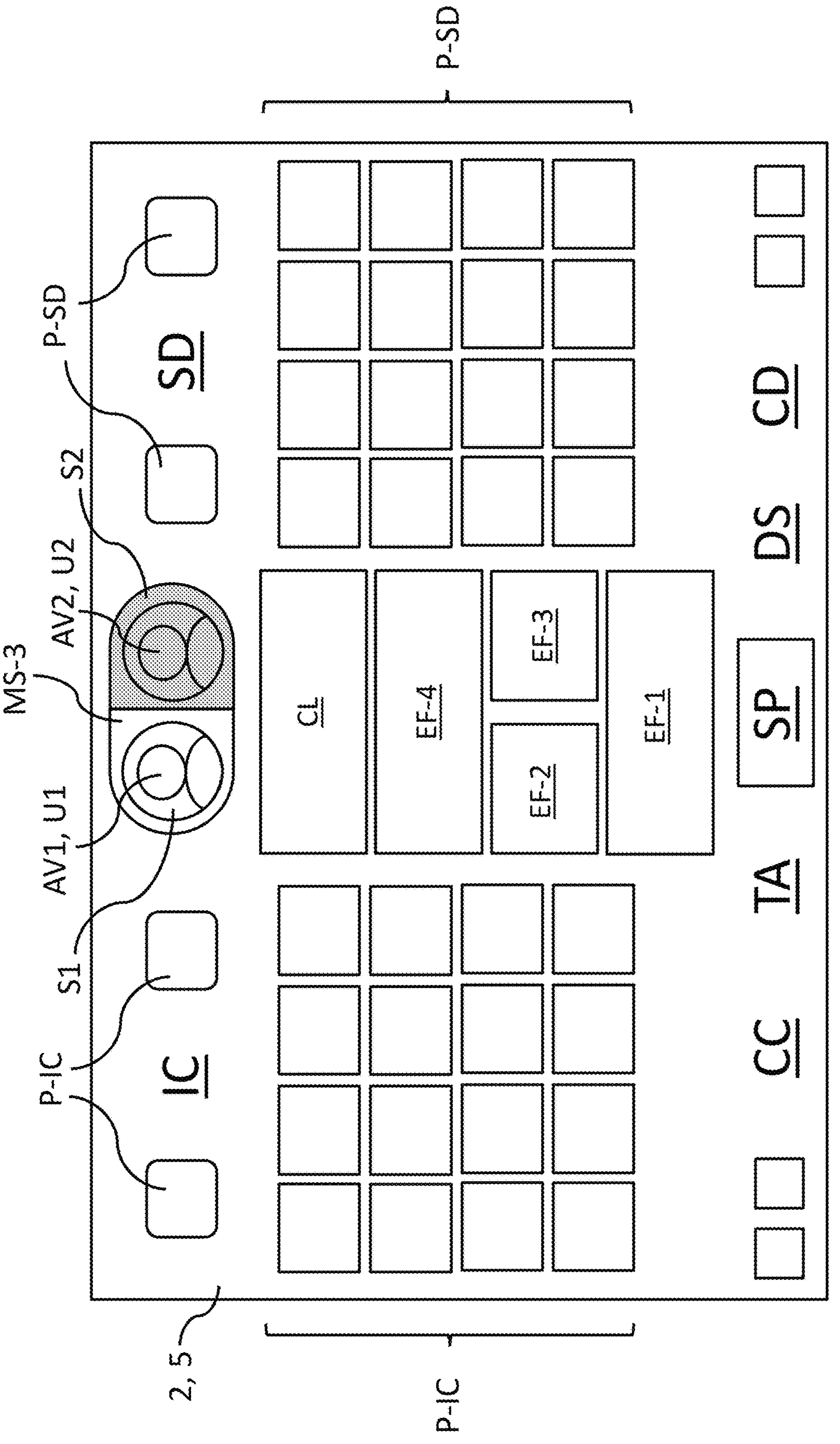

With reference to FIG. 4*d*, a fourth graphic screen which can be displayed on the display module 5 of the exercise machine 1 is shown.

The fourth graphic screen can be displayed on the display module 5 of the exercise machine 1 following the authentication of also at least one second user U2 on the exercise machine 1, upon the selection of a physical exercise from the plurality of physical exercises suggested by the second choice menu M-S2.

The fourth graphic display screen which can be displayed on the display module of the exercise machine 1 comprises a third choice menu MS-3 of which user, among those logged-in on the exercise machine 1, to enable to use the exercise machine for performing the physical exercise.

The third choice menu MS-3 comprises a first selection command S1 corresponding to the first user U1, represented by the first graphic representation (avatar) AV1 of the first user U1, and a second selection command S2 corresponding to the at least one second user U2 represented, in turn, by a second graphic representation (avatar) AV2 of the at least one second user U2.

The fourth graphic screen which can be displayed on the display module 5 of the exercise machine 1 corresponds to when the first user U1 has been selected in the third selection menu MS-3 by pressing the first selection command S1.

Following the selection, the first selection command S1 (together with the first graphic representation (avatar) AV1 of the first user U1) is graphically represented in a different manner with respect to the second selection command S2 (together with the second graphic representation (avatar) AV2 of the at least one second user U2). For example, in the example in FIG. 4*d*, the second selection command S2 is on a gray background or in phantom.

Moreover, the second selection command S2 can comprise an additional graphic symbol (not shown in FIG. 4*d*), superimposed on the second graphic representation (avatar) AV2 of the at least one second user U2, representative of the fact that pressing the second selection command S2 allows the exercise machine 1 to be set from being used by the first user U1 to being used by the at least one second user U2.

The fourth graphic screen which can be displayed on the display module 5 of the exercise machine 1 corresponds to when the first user U1 has selected in the first choice menu M-S1 (FIG. 4*a*) the first physical exercise EF-1, i.e., running on the treadmill.

In this respect, the fourth graphic screen which can be displayed on the display module 5 of the exercise machine 1 thus comprises:

- a first piece of information IC representative of the inclination of the treadmill;
- a second piece of information SD representative of the forward speed of the treadmill;
- a third piece of information TA representative of the running time;
- a fourth piece of information DS representative of the distance traveled;
- a fifth piece of information CD representative of the running pace;
- a sixth piece of information CC representative of calories burned;
- a plurality of pieces of information CL representative of a portion of the run (e.g., one lap within a race involving multiple laps); and
- the physical exercises, in addition to the first physical exercise EF-1, which can be performed by the first user U1 on the treadmill (second physical exercise EF-2: sled training; third physical exercise EF-3: parachute training) and one physical exercise EF-4 which can be performed by the first user U1 when off the treadmill (e.g., bodyweight exercise on the floor).

The fourth graphic screen which can be displayed on the display module 5 of the exercise machine 1 further comprises:

- a plurality of commands P-SD to set the forward speed of the treadmill;
- a plurality of commands P-IC to set the inclination of the treadmill; and
- a stop command SP to stop the treadmill.

Figure 4E:
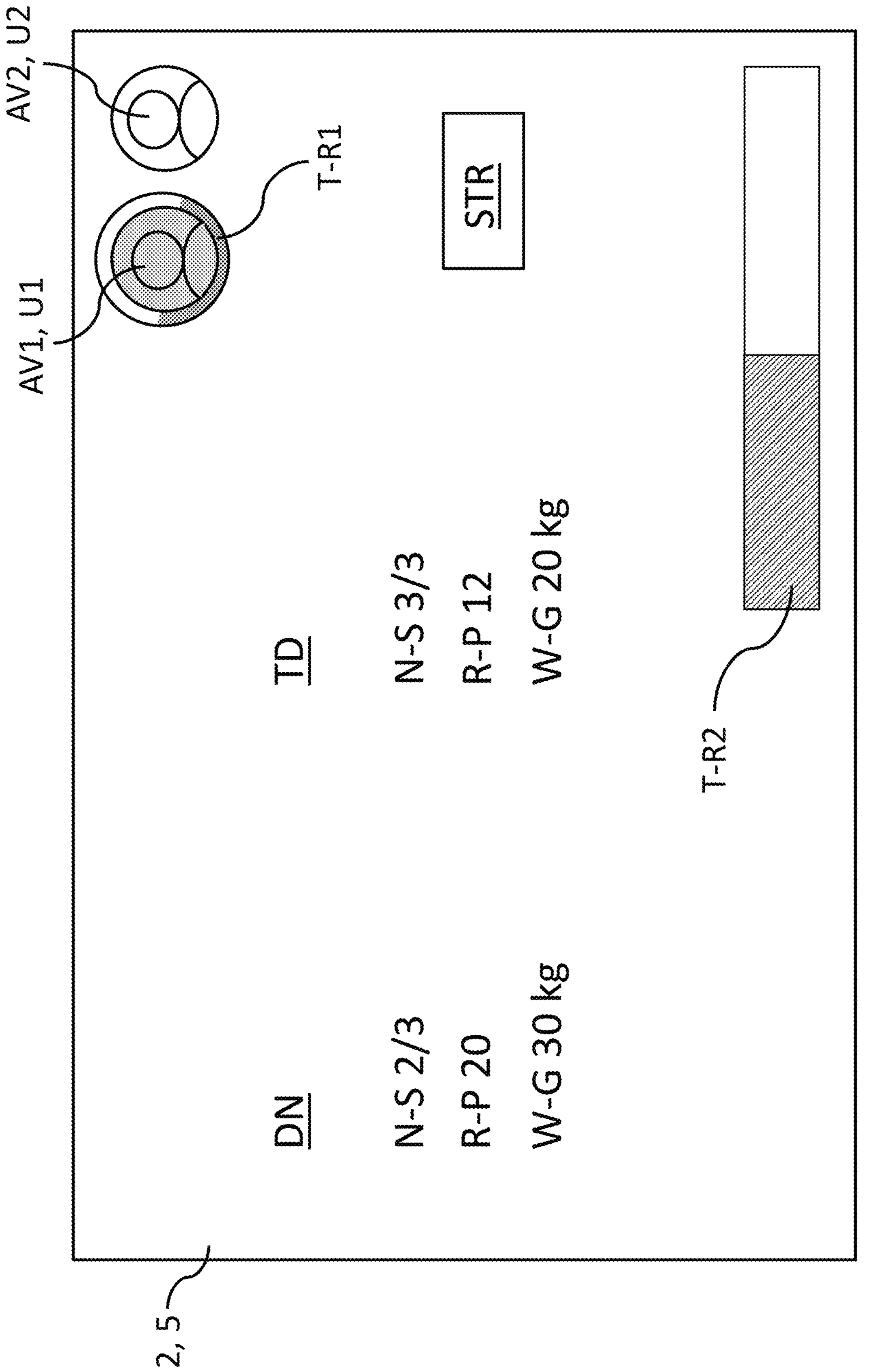
FIGS. 4*e*-4*g* show graphic screens which can be displayed on a display module of a further exercise machine implementing the method for managing the use of an exercise machine by multiple users according to the present invention, during the execution of such a method, and FIG. 5 diagrammatically shows, by means of a block diagram, a method for managing the use of an exercise machine by multiple users for performing a physical exercise, according to the present invention.
Figure 4F:
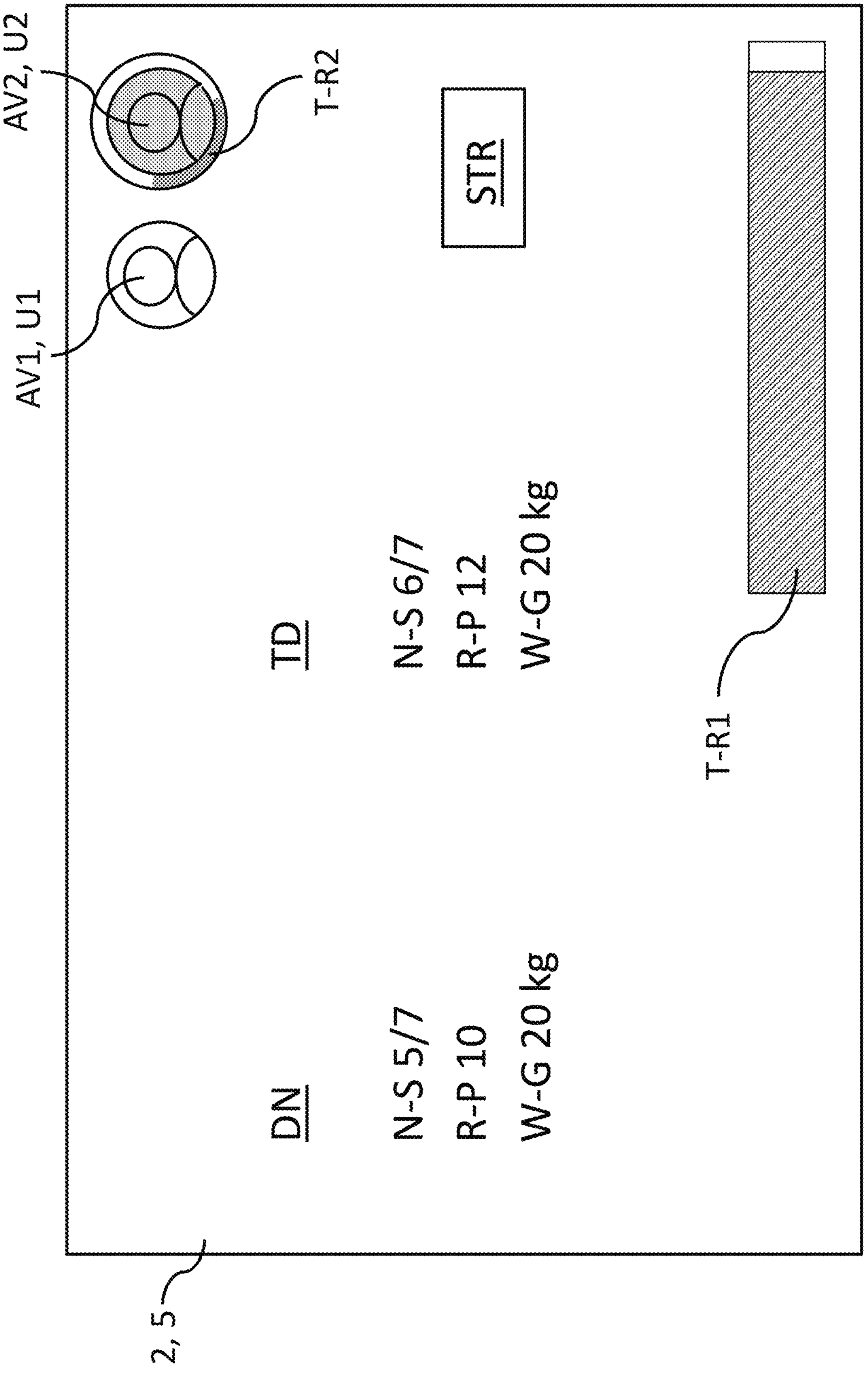
Figure 4G:
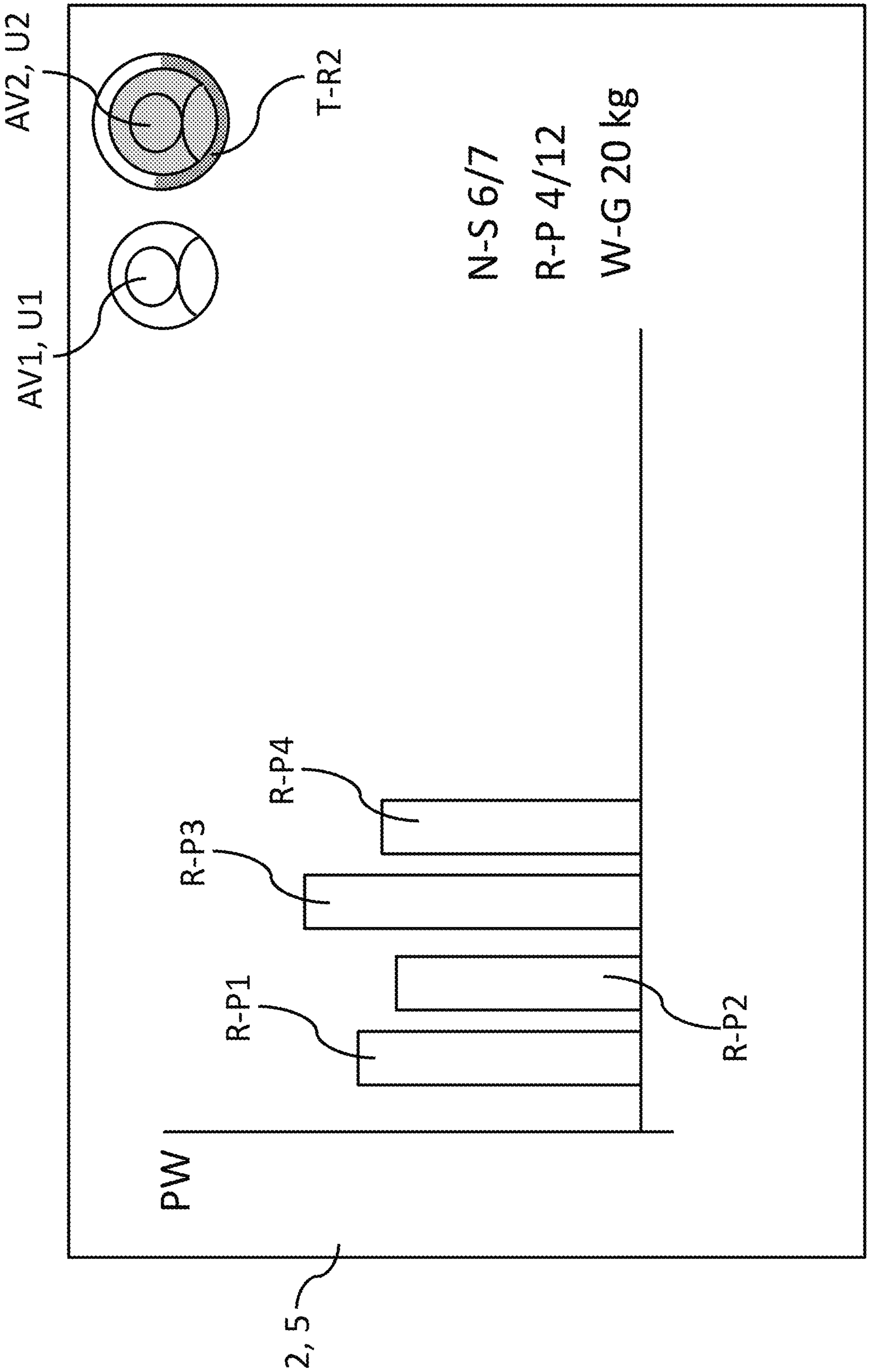

With reference to FIGS. 4*e*-4*g*, further examples of graphic screens which can be displayed on the display module 5 of the exercise machine 1 are now described, when the exercise machine 1 is for muscle strengthening.

It should be noted that these examples also refer to the embodiment of the exercise machine 1 in which the display module 5 coincides with the user interface 2 of the exercise machine 1 which, preferably of the touchscreen type, allows a user to interact with and impart commands to the exercise machine 1.

With reference to FIG. 4*e*, a fifth graphic screen which can be displayed on the display module 5 of the exercise machine 1 is now described.

The fifth graphic screen can be displayed on the display module 5 of the exercise machine 1 following the authentication of both the first user U1 and the at least one second user U2 on the exercise machine 1 and following the selection of the at least one second user U2 for using the exercise machine 1 for the physical exercise.

The fifth graphic screen which can be displayed on the display module 5 of the exercise machine 1 comprises:

- a first graphic representation (avatar) AV1 of the first user U1; and
- a second graphic representation (avatar) AV2 of the at least one second U2 user.

The first graphic representation (avatar) AV1 of the first user U1 (not selected for using the exercise machine 1 for the physical exercise) is graphically represented in a different manner with respect to the second graphic representation (avatar) AV2 of at least one second user U2 (selected for using the exercise machine 1 for the physical exercise). For example, in the example in FIG. 4*e*, the first graphic representation (avatar) AV1 of the first user U1 is on a gray background.

A graphic indication T-R1 representative of the recovery time of the first user U1, e.g., a semicircle adapted to change color clockwise as the recovery time progressively increases.

The fifth graphic screen which can be displayed on the display module 5 of the exercise machine 1 further comprises a first plurality of pieces of information DN representative of the physical exercise performed by the selected user, in this case the at least one second user U2.

The first plurality of pieces of information DN representative of the physical exercise performed by the selected user comprises, for example:

- number of sets N-S performed, e.g., 2 out of 3 (2/3);
- number of repetitions R-P performed for each set, e.g., 20; and
- load value W-G moved, e.g., 30 kg.

The fifth graphic screen which can be displayed on the display module 5 of the exercise machine 1 further comprises a second plurality of pieces of information TD representative of the physical exercise to be performed by the selected user, in this case the at least one second user U2.

The second plurality of pieces of information TD representative of the physical exercise to be performed by the selected user comprises, for example:

- number of sets N-S to be performed, e.g., the third one out of three (3/3);
- number of repetitions R-P to be performed in each set, e.g., 12; and
- load value W-G to be moved, e.g., 20 kg.

The fifth graphic screen which can be displayed on the display module 5 of the exercise machine 1 further comprises:

- an exercise start command STR manually selectable by the at least one second user U2; and
- a graphic indication T-R2 representative of the recovery time of the at least one second user U2, before the start of the exercise to be performed following the selection of the exercise start command STR, e.g., a horizontal bar adapted to change color as the time progressively increases.

With reference to FIG. 4*f*, a sixth graphic screen which can be displayed on the display module 5 of the exercise machine 1 is now described.

The sixth graphic screen can be displayed on the display module 5 of the exercise machine 1 following the authentication of both the first user U1 and the at least one second user U2 on the exercise machine 1 and following the selection of the at least one first user U1 for using the exercise machine 1 for the physical exercise.

The sixth graphic screen which can be displayed on the display module 5 of the exercise machine 1 comprises:

a first graphic representation (avatar) AV1 of the first user U1; and a second graphic representation (avatar) AV2 of the at least one second U2 user.

The first graphic representation (avatar) AV1 of the first user U1 (selected for using the exercise machine 1 for exercise) is graphically represented in a different manner with respect to the second graphic representation (avatar) AV2 of at least one second user U2 (not selected for using the exercise machine 1 for the physical exercise). For example, in the example in FIG. 4*f*, the second graphic representation (avatar) AV2 of the at least one second user U2 is on a gray background.

A graphic indication T-R1 representative of the recovery time of the at least one second user U2, e.g., a semicircle adapted to change color clockwise as the recovery time progressively increases.

The sixth graphic screen which can be displayed on the display module 5 of the exercise machine 1 further comprises the first plurality of pieces of information DN representative of the physical exercise performed by the selected user, in this case the first user U1.

The first plurality of pieces of information DN representative of the physical exercise performed by the selected user comprises, for example:

number of sets N-S performed, e.g., 5 out of 7 (5/7);

number of repetitions R-P performed for each set, e.g., 10; and load value W-G moved, e.g., 20 kg.

The sixth graphic screen which can be displayed on the display module 5 of the exercise machine 1 further comprises the second plurality of pieces of information TD representative of the physical exercise to be performed by the selected user, in this case the first user U1.

The second plurality of pieces of information TD representative of the physical exercise to be performed by the selected user comprises, for example:

number of sets N-S to be performed, e.g., the sixth one out of seven (6/7);

number of repetitions R-P to be performed in each set, e.g., 12; and load value W-G to be moved, e.g., 20 kg.

The sixth graphic screen which can be displayed on the display module 5 of the exercise machine 1 further comprises:

an exercise start command STR manually selectable by the first user U1; and a graphic indication T-R2 of the recovery time of the first user U1, before the start of the exercise to be performed following the selection of the exercise start command STR, e.g., a horizontal bar adapted to change color as the time progressively increases.

With reference to FIG. 4*g*, a seventh graphic screen which can be displayed on the display module 5 of the exercise machine 1 is now described.

The seventh graphic screen can be displayed on the display module 5 of the exercise machine 1 following the selection in the sixth screen in FIG. 4*f*, of the exercise start command STR by the first user U1.

The seventh graphic screen which can be displayed on the display module 5 of the exercise machine 1 comprises:

the first graphic representation (avatar) AV1 of the first user U1; and the second graphic representation (avatar) AV2 of the at least one second U2 user.

The first graphic representation (avatar) AV1 of the first user U1 (selected for using the exercise machine 1 for exercise) is graphically represented in a different manner with respect to the second graphic representation (avatar) AV2 of at least one second user U2 (not selected for using the exercise machine 1 for the physical exercise). For example, in the example in FIG. 4*f*, the second graphic representation (avatar) AV2 of the at least one second user U2 is on a gray background.

A graphic indication T-R2 representative of the recovery time of the at least one second user U2, e.g., a semicircle the color of which changes clockwise as the recovery time progressively increases.

The seventh graphic screen which can be displayed on the display module 5 of the exercise machine 1 further comprises a third plurality of pieces of information DN representative of the physical exercise being performed by the selected user, in this case the first user U1.

The third plurality of pieces of information DN representative of the physical exercise being performed by the selected user comprises, for example:

number of sets N-S being performed, e.g., the sixth one out of seven (6/7);

number of repetitions R-P performed in the set being performed, e.g., 4 out of 12; and load value W-G being moved, e.g., 20 kg.

The seventh graphic screen which can be displayed on the display module 5 of the exercise machine 1 further comprises a plurality of graphic representations R-P1, R-P2, R-P3, RP-4, each corresponding to a repetition performed by the first user U1 since the beginning of the set being performed.

For example, each graphic representation is a rectangle the height of which corresponds to the power value PW generated by the first user U1 in the respective repetition.

Referring now also to FIG. 3, the present invention also relates to a system indicated as a whole by reference numeral 200.

The system 200 comprises at least one exercise machine 1 according to any of the embodiments described above.

The system 200 further comprises a remote electronic processor 100 operatively connected to the data processing unit 3 of the exercise machine 1.

The remote electronic processor 100 is a cloud server, for example.

The remote electronic processor 100 is operatively connected to the data processing unit 3 of the at least one exercise machine 1 by a data communication network (not shown in the figures) in either wired or wireless mode.

Figure 5:
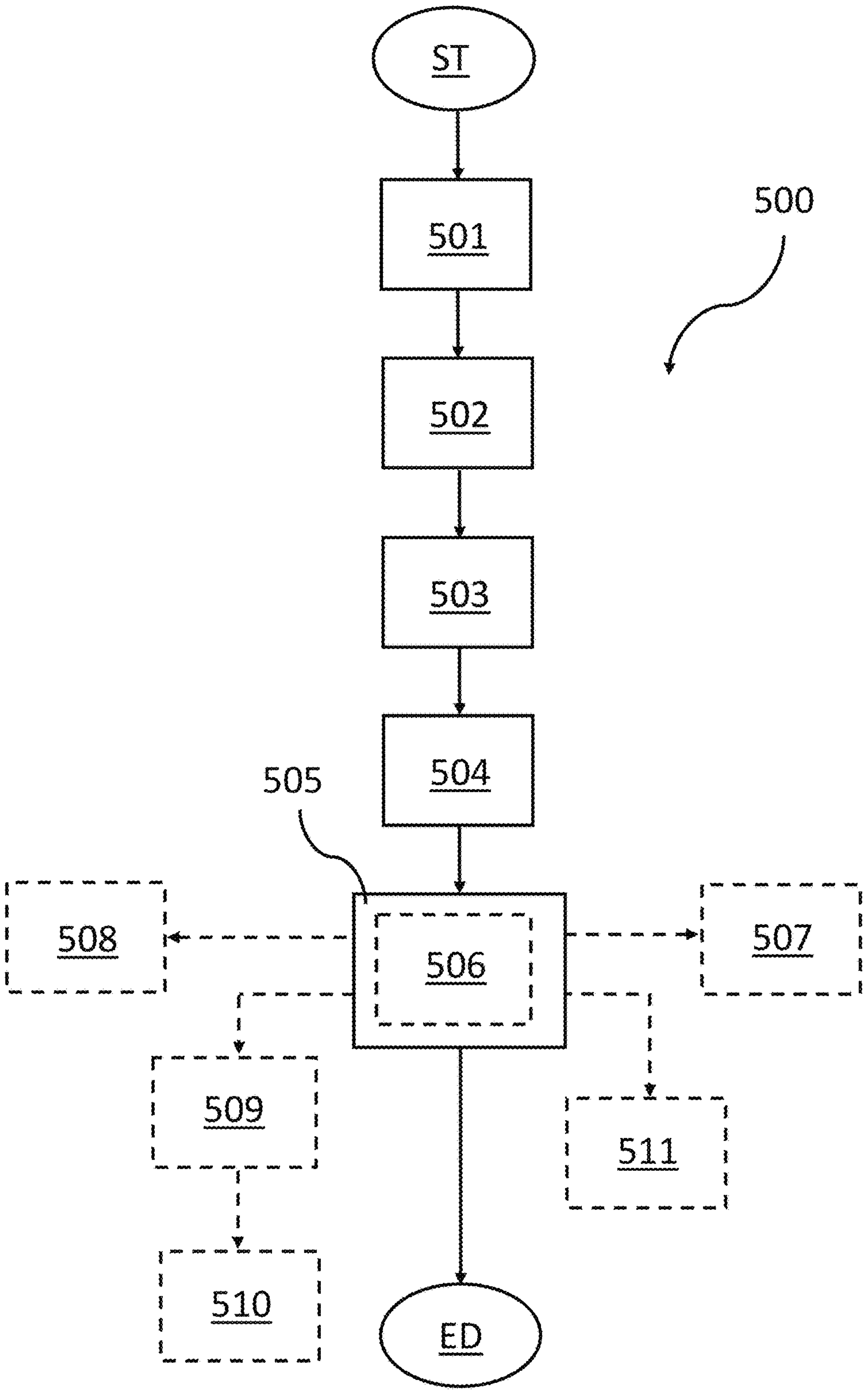

With reference to FIG. 5, a method 500 for managing the use of an exercise machine by multiple users for performing an physical exercise, hereinafter also management method or simply method according to the present invention, is now described.

The exercise machine 1 was described hereinabove according to different embodiments.

The method 500 comprises a symbolic step of starting ST.

The method 500 comprises a step of a1) obtaining 501 from a remote electronic processor 100, by a data processing unit 3 of the exercise machine 1, following an authentication procedure A1 performed on the exercise machine 1 by a first user U1 having a respective user profile, a code CT-1 (for example, an alphanumeric string) identifying the first user U1 and one or more pieces of information representative of the user profile of the first user U1 for using the exercise machine 1 for a respective physical exercise.

The remote electronic processor 100 has already been described hereinabove also with reference to the system 200 diagrammatically shown in FIG. 3.

The method 500 further comprises a step of a2) storing 502 in a local memory unit 4 of the exercise machine 1, by the data processing unit 3 of the exercise machine 1, the obtained code CT-1 identifying the first user U1 and said obtained one or more pieces of information IP-1 representative of the user profile of the first user U1.

The method 500 further comprises a step of b1) obtaining 503 from the remote electronic processor 100, by a data processing unit 3 of the exercise machine 1, following an authentication procedure A-2 performed on the exercise machine 1 by at least one second user U2 having a respective user profile, a code CT-2 identifying the at least one second user U2 and one or more pieces of information IP-2 representative of the user profile of the at least one second user U2 for using the exercise machine 1 for a respective physical exercise.

The method 500 further comprises a step of b2) storing 504 in a local memory unit 4 of the exercise machine 1, by the data processing unit 3 of the exercise machine 1, the obtained code CT-2 identifying the at least one second user U2 and said obtained one or more pieces of information U2 representative of the profile of the at least one second user U2.

The method 500 further comprises a step of c1) setting 505 the exercise machine 1, by the data processing unit 3 of the exercise machine 1, following a selection of one from either the first user U1 or the at least one second user U2 performed on the exercise machine 1, to be used for performing the respective physical exercise by one from either the first user U1 or the at least one second user U2, based on one from either the code CT-1 identifying the first user U1 or the code CT-2 identifying the at least one second user U2 corresponding to the selected user from either the first user U1 or the at least one second user U2.

Again with reference to FIG. 5, the method further comprises a symbolic step of ending ED.

According to an embodiment, in combination with the preceding one and shown by dashed lines in FIG. 5, the step of c1) setting 505 comprises a step of c2) loading 506 on the exercise machine 1 the respective user profile and a respective physical exercise program corresponding to the selected user from either the first user U1 or the at least one second user U2, based on the one from either the code CT-1 identifying the first user U1 or the code CT-2 identifying the at least one second user U2 corresponding to the selected user from either the first user U1 or the at least one second user U2.

According to an embodiment, in combination with any of the preceding ones and shown by dashed lines in FIG. 5, the method 500 further comprises a step of d1) querying 507 the remote electronic processor 100 during the use of the exercise machine 1 for performing the respective physical exercise by the selected user from either the first user U1 or the at least one second user U2, using the one from either the code CT-1 identifying the first user or the code CT-2 identifying the at least one second user U2 corresponding to the selected user from either the first user U1 or the at least one second user U2, stored in the local memory unit 4 of the exercise machine 1.

In greater detail, the step of querying 507 the remote electronic processor 100 is performed by the data processing unit 3 of the exercise machine 1 in real time, at set instants of sampling time, to retrieve setting and control data of the exercise machine 1 provided by the training program running while the selected user performs the physical exercise.

According to an embodiment, in combination with any of the preceding ones and shown by dashed lines in FIG. 5, the method 500 further comprises a step of e1) storing 508, by the data processing unit 3 of the exercise machine 1, during the use of the exercise machine 1, data representative of the respective physical exercise performed by the user with the exercise machine 1.

According to an embodiment, in combination with the preceding one, the step of e1) storing 508 data representative of the respective physical exercise performed by the user with the exercise machine 1 is carried out, by the data processing unit 3 of the exercise machine 1, for storing the data representative of the respective physical exercise performed by the user with the exercise machine 1 in the local memory unit 4 of the exercise machine 1 and/or in the remote electronic processor 100 based on the identification code from either the code CT-1 identifying the first user U1 or the code CT-2 identifying the at least one second user U2 corresponding to the selected user.

In greater detail, the identification code is also used to identify the storage location of the data to be stored, for example, the storage location in the local memory unit 4 of the exercise machine 1 or the storage location in the remote electronic processor 100 associated with the user's account.

According to an embodiment, in combination with the preceding one and shown by dashed lines in FIG. 5, the step of e1) storing 508 data representative of the respective physical exercise performed by the user with the exercise machine 1 is carried out, by the data processing unit 3 of the exercise machine 1, for storing data representative of a group of movements provided by the physical exercise performed by the user with the exercise machine 1 from when the data processing unit 3 of the exercise machine has selected such a user from either the first user U1 or the at least one second user U2, for using the exercise machine 1 to when the data processing unit 3 of the exercise machine 1 has then selected the other user from either the first user U1 or the at least one second user U2 for using the exercise machine 1.

According to an embodiment, in combination with any of the preceding ones and shown by dashed lines in FIG. 5, if the user, either the first user U1 or the at least one second user U2, has already been selected once for using the exercise machine 1 and has performed a first group of movements provided by the exercise performed by the selected user and the data processing unit 3 of the exercise machine 1 has stored first data representative of the first group of movements provided by the physical exercise performed by the selected user, the method 500 comprises steps of:

- retrieving 509, by the data processing unit 3 of the exercise machine 1, when the data processing unit 3 of the exercise machine 1 selects the user again from either the first user U1 or the at least one second user U2 for using the exercise machine 1, the previously stored first data representative of the first group of movements provided by the physical exercise performed by the selected user;
- setting 510 the exercise machine 1, by the data processing unit 3 of the exercise machine 1, to be used for performing a second group of movements provided by the physical exercise performed by the selected user, based on the previously stored first data representative of the first group of movements provided by the physical exercise performed by the selected user.

According to an embodiment, in combination with any of the preceding ones, the selection of either the first user U1 or the at least one second user U2 is carried out by the data processing unit 3 of the exercise machine 1 based on a received manual command.

According to an embodiment, in combination with any of the preceding ones, the selection of the one from the first user U1 or the at least one second user U2 is automatically carried out by the data processing unit 3 of the exercise machine 1 based on a set workout program provided for the first user U1 and a set workout program U2 provided for the at least one second user U2.

In other words, from the set training programs provided for the first user U1 and for the at least one second user U2, the data processing unit 3 is able of automatically selecting one of the first user U1 and the at least a second U2 user.

For example, once the first user U1 completes the assigned repetitions (provided by the set training program) on a strength exercise machine or completes an assigned distance to walk (provided by the set training program) on a treadmill, the data processing unit 3 is able of automatically selecting the at least one second user U2.

According to a further embodiment, in combination with any of the preceding ones, the selection of either the first user U1 or the at least one second user U2 is carried out automatically by the data processing unit 3 of the exercise machine 1 if only one of the first user U1 or the at least one second user U2 (e.g., the first user U1) has already performed the authentication procedure on the exercise machine 1 and the other of either the first user U1 or the at least one second user U2 (e.g., the at least one second user U2) performs the authentication procedure on the exercise machine 1 for the first time.

In other words, the data processing unit 3 is able of automatically selecting one of the first user U1 and the at least one second user U2 if one of the first user U1 and the at least one second user U2 (for example, the at least one second user U2) performs the authentication procedure on the exercise machine 1 for the first time while only the other between the first user U1 and the at least one second user U2 (for example, the first user U1) has already carried out the authentication procedure on exercise machine 1.

In this case, following the first authentication of the at least one second user U2, the data processing unit 3 of the exercise machine 1 automatically sets the user profile corresponding to the at least one second user U2 on the exercise machine 1.

According to a further embodiment, in combination with any of the preceding ones, the selection of either the first user U1 or the at least one second user U2 is carried out automatically by the data processing unit 3 of the exercise machine 1 if both the first user U1 and the at least one second user U2 have performed the authentication procedure on the exercise machine 1 and either the first user U1 or the at least one second user U2 performs a log-out procedure from the exercise machine 1.

In other words, if both the first user U1 and the at least one second user U2 are authenticated on the exercise machine 1 and one of the first user U1 and the at least one second user U2 executes the log-out procedure, the data processing unit 3 is configured to automatically perform the selection of the other between the first user U1 and the at least one second user U2 so as to maintain the setting of the exercise machine 1 for the user who remained authenticated.

In this way, optimal and optimized use of the exercise machine 11 is guaranteed.

For example, if the first user U1 performs the log-out procedure, the data processing unit 3 of the exercise machine 1 is configured to select the at least one second user U2 and automatically set the user profile corresponding to the at least one second user U2 on the exercise machine 1.

According to an embodiment, in combination with the preceding one, if there are multiple users logged-in on the exercise machine 1, in addition to the first user U1 and the at least one second user U2, the selection of one of the users who have performed the authentication procedure on the exercise machine 1 is carried out automatically by the data processing unit 3 of the exercise machine 1 if one of the users performs a log-out procedure from the exercise machine 1 on the exercise machine 1, based on a set priority criterion.

For example, the data processing unit 3 of the exercise machine 1 can automatically select the user, from those remaining logged in on the exercise machine 1, who had first performed the authentication procedure.

According to an embodiment, in combination with any of the preceding ones and shown by dashed lines in FIG. 5, the method 500 comprises a step of performing 511 a log-out procedure from the exercise machine, by the data processing unit 3 of the exercise machine 1, for both the first user U1 and the at least one second user U2.

According to an embodiment, in combination with the preceding one and shown by dashed lines in FIG. 5, the log-out procedure is performed, by the data processing unit 3 of the exercise machine 1, simultaneously for the first user U1 and the at least one second user U2.

According to an embodiment, as an alternative to the preceding one and shown by dashed lines in FIG. 5, the log-out procedure is performed, by the data processing unit 3 of the exercise machine 1, at different time instants for the first user U1 and the at least one second user U2.

A first example of implementation of the method for managing the use of an exercise machine by multiple users according to the present invention is now described with reference to the figures.

A first user U1 having a first user profile logs-in on an exercise machine 1, e.g., a treadmill (FIG. 4*a*).

Following the authentication procedure A-1 of the first user U1, a data processing unit 3 of the exercise machine 1 obtains from a remote electronic processor 100 a code CT-1 identifying the first user and one or more pieces of information representative of the user profile of the first user for using the exercise machine for a respective physical exercise.

The data processing unit 3 of the exercise machine 1 stores, in a data local memory 4 of the exercise machine 1, the obtained code CT-1 identifying the first user U1 and said obtained one or more pieces of information IP-1 representative of the user profile of the first user U1.

A second user U2 having a second user profile is added on the exercise machine 1 and logs-in on the exercise machine 1 (FIG. 4*b*).

Following the authentication procedure A-2 of the second user U2, the data processing unit 3 of the exercise machine 1 obtains from the remote electronic processor 100 an identification code CT-2 of the second user U2 and one or more pieces of information IP-2 representative of the user profile of the second user U2 for using the exercise machine 1 for a respective physical exercise.

The data processing unit 3 of the exercise machine 1 stores, in the local memory unit 4 of the exercise machine 1, the obtained code CT-2 identifying the second user U2 and said obtained one or more one or more pieces of information U2 representative of the second user U2.

The first user U1 is selected on the display module 5 of the exercise machine 1 from the first user U1 and the at least one second user U2 (FIG. 4*c*).

The data processing unit 3 of the exercise machine 1 sets the exercise machine 1 to be used for performing the respective physical exercise by the first user U1 based on the code CT-1 identifying the first user U1.

The first user U1 works out on the exercise machine 1 (treadmill) by running (with set speed and inclination) based on his/her physical exercise program while the second user U2, based on his/her physical exercise program, works out on the floor, e.g., performing a set of repetitions of lunges with equipment.

After a period of time set by the physical exercise program has elapsed, the second user U2 is then selected on the display module 5 of the exercise machine 1.

The data processing unit 3 of the exercise machine 1 sets the exercise machine 1 to be used for performing the respective physical exercise by the second user U2 based on the code CT-2 identifying the second user U2.

The second user U2 works out on the exercise machine 1 (treadmill) by running (with set speed and inclination) based on his/her physical exercise program while the first user U1, based on his/her physical exercise program, works out on the floor, e.g., performing a set of repetitions of lunges with equipment.

After a period of time provided by the physical exercise program has elapsed, the first user U1 is then selected on the display module 5 of the exercise machine 1 again.

The data processing unit 3 of the exercise machine 1 sets the exercise machine 1 to be used for performing the respective exercise by the first user U1 based on the code CT-1 identifying the first user U1, allowing the first user U1 to retrieve the data and continue his/her physical exercise on the exercise machine 1 from the point in which he/she had arrived at the time the second user U2 was selected.

The first user U1 works out on the exercise machine 1 (treadmill) with a pushing exercise based on his/her physical exercise program while the second user U2, based on his/her physical exercise program, works out on the floor, e.g., performing a set of repetitions of lifts with equipment.

After a period of time provided by the physical exercise program has elapsed, the second user U2 is then selected on the display module 5 of the exercise machine 1 again.

The data processing unit 3 of the exercise machine 1 sets the exercise machine 1 to be used for performing the respective physical exercise by the second user U2 based on the code CT-2 identifying the second user U2, allowing the second user U2 to retrieve the data to continue what he/she left off the previous time the exercise machine 1 was used.

The second user U2 works out on the exercise machine 1 (treadmill) with a pushing physical exercise based on his/her exercise program while the first user U1, based on his/her exercise program, works out on the floor, e.g., performing a set of repetitions of lifts with equipment.

At the end of the physical exercise program of both the first user U1 and the second user U2, the data processing unit 3 of the exercise machine 1 performs a simultaneous log-out procedure for both users.

If the exercise machine 1 is a strength exercise machine, a first user U1 and at least one second user U2 can log-in on the exercise machine 1 as described above.

The first user U1 is selected on the display module 5 of the exercise machine 1 from the first user U1 and the at least one second user U2 (FIG. 4*f*).

The data processing unit 3 of the exercise machine 1 sets the exercise machine 1 to be used for performing the respective physical exercise by the first user U1 based on the code CT-1 identifying the first user U1.

The first user U1 selects an exercise start command STR (FIG. 4*f*) and works out on the exercise machine 1 (strength exercise machine) with a set of repetitions based on his/her physical exercise program while the at least one second user U2 recovers and waits for his/her turn (FIG. 4*g*).

After a period of time set by the physical exercise program has elapsed, the at least one second user U2 is then selected on the display module 5 of the exercise machine 1.

The data processing unit 3 of the exercise machine 1 sets the exercise machine 1 to be used for performing the respective physical exercise by the at least one second user U2 based on the code CT-2 identifying the at least one second user U2.

The at least one second user U2 works out on the exercise machine 1 (strength exercise machine) with a set of repetitions based on his/her physical exercise program while the first user U1 recovers and waits for his/her turn.

It should be noted that according to which user is selected, the display module 5 of the exercise machine 1 will show the workout data of the selected user only.

At the end of the physical exercise program of the first user U1, the data processing unit 3 of the exercise machine 1 performs a log-out procedure for the first user U1.

At the end of the physical exercise program of the at least one second user U2, the data processing unit 3 of the exercise machine 1 also performs a log-out procedure for the at least one second user U2.

As can be seen, the object of the invention is fully achieved.

Indeed, the method and the related exercise machine of the present invention allow using the exercise machine by multiple users in a simple, user-friendly and especially timely manner, ensuring that each user's workout is as high-performing as possible.

Indeed, the storing of temporary identification codes for each logged-in user allows quickly setting the exercise machine for performing the physical exercise by the selected user without needing to carry out an authentication procedure again, whenever the user selects or is selected for the uses of the exercise machine.

Moreover, whenever a user uses an exercise machine again to continue the physical exercise, being able to retrieve the workout data previously stored when the physical exercise machine was previously used advantageously allows increasing the workout efficiency and achievable performance.

Those skilled in the art may make changes and adaptations to the embodiments of the method and exercise machine described above or can replace elements with others which are functionally equivalent in order to meet contingent needs without departing from the scope of the following claims. Each of the features described above as belonging to a possible embodiment may be implemented irrespective of the other embodiments described.

What is claimed is:

1. A method for managing the use of an exercise machine by multiple users for performing physical exercises, comprising steps of:

a1) obtaining from a remote electronic processor, by a data processing unit of the exercise machine, following an authentication procedure performed on the exercise machine by a first user having a respective user profile, a code identifying the first user and one or more pieces of information representative of the user profile of the first user for using the exercise machine for a respective physical exercise;

a2) storing in a local memory unit of the exercise machine, by the data processing unit of the exercise machine, the obtained code identifying the first user and said obtained one or more pieces of information representative of the user profile of the first user;

b1) obtaining from the remote electronic processor, by the data processing unit of the exercise machine, following an authentication procedure performed on the exercise machine by at least one second user having a respective user profile, a code identifying the at least one second user and one or more pieces of information representative of the user profile of the at least one second user for using the exercise machine for a respective physical exercise;

b2) storing in the local memory unit of the exercise machine, by the data processing unit of the exercise machine, the obtained code identifying the at least one second user and said obtained one or more pieces of information representative of the user profile of at least one second user; and c1) setting the exercise machine, by the data processing unit of the exercise machine, following a selection of either the first user or the at least one second user performed on the exercise machine to be used for performing the respective physical exercise by either the first user or the at least one second user, based on either the code identifying the first user or the code identifying the at least one second user corresponding to a selected user of either the first user or the at least one second user;

performing a log-out procedure on the exercise machine, by the data processing unit of the exercise machine, for both the first user and the at least one second user.

2. The method of claim 1, wherein step c1) comprises a step of c2) loading on the exercise machine the respective user profile and a respective physical exercise program corresponding to the selected user of either the first user or the at least one second user, based on either the code identifying the first user or the code identifying the at least one second user corresponding to the selected user of either the first user or the at least one second user.

3. The method of claim 1, further comprising a step of d1) querying the remote electronic processor during use of the exercise machine for performing the respective physical exercise by the selected user of either the first user or the at least one second user, using either the code identifying the first user or the code identifying the at least one second user corresponding to the selected user of either the first user or the at least one second user, stored in the local memory unit of the exercise machine.

4. The method of claim 1, further comprising a step of e1) storing, by the data processing unit of the exercise machine, during use of the exercise machine, data representative of the respective physical exercise performed by the user with the exercise machine.

5. The method of claim 4, wherein the step of storing data representative of the respective physical exercise performed by the user with the exercise machine is performed, by the data processing unit of the exercise machine, for storing the data representative of the respective physical exercise performed by the user with the exercise machine in the local memory unit of the exercise machine and/or in the remote electronic processor based on an identification code selected from the code identifying the first user and the code identifying the at least one second user corresponding to the selected user.

6. The method of claim 5, wherein the step of storing data representative of the respective physical exercise performed by the user with the exercise machine is performed, by the data processing unit of the exercise machine, for storing data representative of a group of movements provided by the physical exercise performed by the user with the exercise machine from a moment in which the data processing unit of the exercise machine selected a user between the first user and the at least one second user, for using the exercise machine to a later moment in which the data processing unit of the exercise machine selected the other user between the first user and the at least one second user for using the exercise machine.

7. The method of claim 4, wherein, if a user, between the first user and the at least one second user has already been selected once for using the exercise machine and has performed a first group of movements provided by the physical exercise performed by the selected user and the data processing unit of the exercise machine has stored first data representative of the first group of movements provided by the physical exercise performed by the selected user, the method comprises steps of:

retrieving, by the data processing unit of the exercise machine, in a moment in which the data processing unit of the exercise machine selects a user again between the first user and the at least one second user, for using of the exercise machine, the first data previously stored representative of the first group of movements provided by the physical exercise performed by the selected user; and setting the exercise machine, by the data processing unit of the exercise machine, for use for performing a second group of movements provided by the physical exercise performed by the selected user, based on the first data previously stored representative of the first group of movements provided by the physical exercise performed by the selected user.

8. The method of claim 1, wherein either the first user or the at least one second user is selected by the data processing unit of the exercise machine based on a received manual command.

9. The method of claim 1, wherein either the first user or the at least one second user is selected automatically by the data processing unit of the exercise machine based on a set workout program provided for the first user and a set workout program provided for the at least one second user.

10. The method of claim 1, wherein either the first user or the at least one second user is selected automatically by the data processing unit of the exercise machine if both the first user and the at least one second user have performed the authentication procedure on the exercise machine and either the first user or the at least one second user performs a log-out procedure from the exercise machine.

11. The method of claim 1, wherein the log-out procedure is performed, by the data processing unit of the exercise machine at the same time for the first user and the at least one second user.

12. The method of claim 1, wherein the log-out procedure is performed, by the data processing unit of the exercise machine, at different instants of time for the first user and the at least one second user.

13. An exercise machine comprising:

a data processing unit;

a memory local unit operatively associated with the data processing unit, the data processing unit being configured to perform the steps of the method of claim 1.

14. A system comprising:

an exercise machine according to claim 13; and a remote electronic processor operatively connected to the data processing unit of the exercise machine.

* * * * *